(12) United States Patent
Azouz et al.

(10) Patent No.: US 10,821,094 B2
(45) Date of Patent: Nov. 3, 2020

(54) COMPOSITIONS AND METHODS FOR TREATING ALLERGIC INFLAMMATORY CONDITIONS

(71) Applicant: CHILDREN'S HOSPITAL MEDICAL CENTER, Cincinnati, OH (US)

(72) Inventors: Nurit P. Azouz, Cincinnati, OH (US); Marc E. Rothenberg, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 16/069,412

(22) PCT Filed: Dec. 22, 2016

(86) PCT No.: PCT/US2016/068238
§ 371 (c)(1),
(2) Date: Jul. 11, 2018

(87) PCT Pub. No.: WO2017/123401
PCT Pub. Date: Jul. 20, 2017

(65) Prior Publication Data
US 2019/0000799 A1    Jan. 3, 2019

Related U.S. Application Data

(60) Provisional application No. 62/278,246, filed on Jan. 13, 2016.

(51) Int. Cl.
| | | |
|---|---|---|
| *A61K 38/55* | (2006.01) | |
| *A61K 38/57* | (2006.01) | |
| *A61K 31/37* | (2006.01) | |
| *A61K 31/711* | (2006.01) | |
| *A61P 37/08* | (2006.01) | |
| *A61K 31/7105* | (2006.01) | |
| *C12N 15/113* | (2010.01) | |

(52) U.S. Cl.
CPC ............ *A61K 31/37* (2013.01); *A61K 31/711* (2013.01); *A61K 31/7105* (2013.01); *A61K 38/55* (2013.01); *A61K 38/57* (2013.01); *A61P 37/08* (2018.01); *C12N 15/113* (2013.01)

(58) Field of Classification Search
CPC ................................ A61K 38/55; A61K 38/57
See application file for complete search history.

(56) References Cited

U.S. PATENT DOCUMENTS

| | | | | |
|---|---|---|---|---|
| 5,412,073 A   * | 5/1995 | Kalsheker | .......... | C07K 14/8125 530/350 |
| 2011/0144183 A1* | 6/2011 | Paquet | ............... | A61K 31/7088 514/44 A |
| 2014/0073801 A1* | 3/2014 | Storer | .................. | C07D 207/16 548/537 |
| 2014/0228301 A1* | 8/2014 | Meade | ................... | A61K 38/57 514/20.9 |
| 2015/0182499 A1 | 7/2015 | Rebound-Ravaux et al. | | |
| 2015/0355180 A1 | 12/2015 | Resnick et al. | | |
| 2019/0046444 A1* | 2/2019 | Konduri | ................. | A61K 9/127 |

OTHER PUBLICATIONS

Spergel et al. Treatment of eosinophilic esophagitis with specific food elimination diet directed by a combination of skin prick and patch tests. Annals of Allergy, Asthma & Immunology. Oct. 2005, vol. 95, pp. 336-343. (Year: 2005).*
Liesveld, "Hypereosinophilic Syndrome". Dec. 2018, Merck Manual Professional Version (5 pages). (Year: 2018).*
Rahaghi et al. Long-term clinical outcomes following treatment with alpha 1-proteinase inhibitor for COPD associated with alpha-1 antitrypsin deficiency: a look at the evidence. Respiratory Research. 2017, vol. 18:105 (9 pages).—(Year: 2017).*
Weber et al, Abstract-Characterization of the protease inhibitor SPINK7 in human skin, 41st Annual Meeting of the Arbeitsgemeinschaft Dermatolgische Forschung, Experiemental Dermatology, Mar. 13-15, 2014, vol. 23, pp. 1-52.
International Search Report and Written Opinion of the International Searching Authority dated Mar. 27, 2017 for International Application No. PCT/US2016/068238, filed Dec. 22, 2016, 8 pages.
Azouz, N. et al., (2016). "Loss of SPINK7 in esophageal epithelial cells unleashes a pro-inflammatory response characterized by excessive cytokine production and loss of barrier function." *J. Allergy Clin. Immunol.* 137(2) Suppl. p. AB280 #915. 1 page.
Azouz, N. et al., (Jun. 6, 2018). "The antiprotease SPINK7 serves as an inhibitory checkpoint for esophageal epithelial inflammatory responses." *Sci. Transl. Med.* 10(444): doi:10.1126/scitranslmed. aap9736. 29 pages.
Valeska, H. et al., (May 2019). "Wheat amylase/trypsin inhibitors aggravate eosinophilic esophagitis." *Gastroenterol.* 156(6, Suppl. 1) S619. 1 page.
Von Arnim, U. et al., (2014). "Eosinophilic esophagitis-treatment of eosinophil esophagitis with drugs: corticosteroids." *Digestive Diseases* 32:126-129.
Extended European Search Report dated Jul. 23, 2019 for International Application No. PCT/US2016/068238, filed Dec. 22, 2016, 15 pages.

* cited by examiner

*Primary Examiner* — Jeffrey E. Russel
(74) *Attorney, Agent, or Firm* — Muriel Liberto, Esq.; Mintz Levin Cohn Ferris Glovsky and Popeo, P.C.

(57) ABSTRACT

The invention provides methods of treating an allergic inflammatory condition characterized by inflammation of a squamous epithelium in a target tissue using alpha-1 proteinase inhibitors to replenish SPINK7 protein and/or SPINK7 anti-proteinase activity in the target tissue, and related methods and compositions.

6 Claims, 20 Drawing Sheets

3-(3-chlorophenyl)carboxy-7-hydroxymethyl coumarin $IC_{50} = 52 \pm 12$ µM (lit. 94 nM)

II
3-carboxy-7-hydroxymethyl coumarin

COMPOSITIONS AND METHODS FOR TREATING ALLERGIC INFLAMMATORY CONDITIONS

CROSS-REFERENCE TO RELATED APPLICATIONS

This application is a national stage entry, filed under 35 U.S.C. § 371, of International Application No. PCT/US2016/068238, filed on Dec. 22, 2016, which claims the benefit of U.S. Provisional Patent Application No. 62/278,246, filed Jan. 13, 2016, the content of which is incorporated herein by reference in its entirety.

FIELD OF THE INVENTION

The invention disclosed herein generally relates to compositions and methods for treating an allergic inflammatory condition.

BACKGROUND

Epithelial barrier impairment has been implicated in the development of allergic disease. However, the molecular mechanisms by which impaired epithelial barrier function induces Th2-type immune responses remain largely unknown.

Epithelial cells are uniquely positioned as the first line of defense against type-2 (Th2)-cell-mediated immune insults (Hammad, H. & Lambrecht, B. N. *Immunity* 43, 29-40 (2015)). In response to perturbation of barrier integrity, acute injury and/or immune stimulation, epithelial cells secrete discrete pro-inflammatory cytokines such as interleukin-1 (IL-1), IL-25, IL-33, and TSLP, which prime dendritic cells to promote Th2 immune responses (Hammad, H. & Lambrecht, B. N. *Immunity* 43, 29-40 (2015)). The esophageal epithelium is comprised of non-keratinized stratified squamous cells, including a layer of mitotically-active cells (stratum basalis), several layers of actively transporting cells (stratum spinosum), and the most luminal layers (stratum corneum) comprised of apical cell membranes, apical junctional complexes, and a matrix of glycoproteins and structural proteins such as filaggrin that together provide a tight epithelial barrier which allows sampling but not penetration of external antigens (Orlando, R. C. *Best practice & research. Clinical gastroenterology* 24, 873-882).

The importance of loss of barrier integrity in eliciting Th2 responses is illustrated by predisposition to atopy in individuals harboring loss of function mutations in the proteinase inhibitor SPINK5. Homozygous loss of SPINK5 results in uncontrolled proteolytic activity in the skin which leads to barrier defect and atopy. An imbalance between SPINK5 and proteinases has been proposed to contribute to the pathogenesis of atopic dermatitis (AD) (Furio, L. et al. *The Journal of experimental medicine* 211, 499-513). Whether a similar process is generalizable to other inflammatory diseases has not been demonstrated.

Eosinophilic esophagitis (EoE) is an inflammatory Th2 type immune disease of the esophagus. EoE is considered to be a chronic immune system disease. Although it was identified only during the last twenty years, it is now considered a major cause of digestive system (gastrointestinal) illness. In EoE, eosinophils (a type of white blood cell) build up in the lining of the esophagus. This buildup, which may be a reaction to foods, allergens or acid reflux, can inflame and/or injure the esophageal tissue. Damaged esophageal tissue can lead to difficulty swallowing or lead to other complications. Symptoms include difficulty swallowing (dysphagia), food impaction, chest pain that is often centrally located and does not respond to antacids, persistent heartburn, upper abdominal pain, lack of response to gastroesophageal reflux disease (GERD) medication, and backflow of undigested food (regurgitation).

Current clinical standards for diagnosis of EoE include (i) endoscopy to inspect the lining of the esophagus for inflammation and swelling, horizontal rings, vertical furrows, narrowing (strictures) and white spots; (ii) biopsy of esophageal tissue with one biopsy showing more than 15 eosinophils per high power field in patients using a proton pump inhibitor (PPI) for approximately 8 weeks.

Treatment for EoE that is not responsive to PPIs includes an orally administered topical steroid, such as fluticasone or budesonide. Where topical steroids prove ineffective, prednisone may be prescribed. There is a need for new treatment options for EoE and similar allergic inflammatory disorders characterized by inflammation of squamous epithelium. The present disclosure addresses this need.

SUMMARY OF THE INVENTION

The present disclosure generally provides methods of treating an allergic inflammatory condition in a subject in need thereof, the allergic inflammatory condition characterized by inflammation of a squamous epithelium in a target tissue of the subject, by replenishing SPINK7 protein and/or SPINK7 anti-proteinase activity in the target tissue. In embodiments, the target tissue is esophageal tissue and the methods are for treating EoE.

In embodiments, the disclosure provides methods of treating an allergic inflammatory condition in a subject in need thereof, the allergic inflammatory condition characterized by inflammation of a squamous epithelium in a target tissue of the subject, the method comprising administering to the subject a pharmaceutical composition comprising an amount of a therapeutic agent effective to replenish SPINK7 protein and/or SPINK7 anti-proteinase activity in the target tissue. In embodiments, the squamous epithelium is of esophageal tissue. In embodiments, the allergic inflammatory condition is esophageal eosinophilia (EE) or eosinophilic esophagitis (EoE).

In embodiments, the therapeutic agent is a serine proteinase inhibitor. In embodiments, the therapeutic agent is an alpha-1 proteinase inhibitor. In embodiments, the alpha-1 proteinase inhibitor is an alpha-1 antitrypsin (A1AT) inhibitor.

In embodiments, the therapeutic agent is an inhibitor of urokinase plasminogen activator (uPA) or kallikrein 5 (KLK5) in the target tissue. In embodiments, the therapeutic agent is a proteinase inhibitor, a KLK5-Fc fusion protein, a KLK5 anti-sense polynucleotide, a KLK5-directed miRNA, a KLK5-directed shRNA, or a KLK5-directed antibody. In embodiments, the therapeutic agent is selected from 3-(3-chlorophenyl)carboxy-7-hydroxymethyl courmarin or 3-carboxy-7-hydroxymethyl coumarin.

In embodiments, the therapeutic agent comprises a recombinant mRNA encoding a SPINK7 protein, or a recombinant SPINK7 polypeptide. In embodiments, the therapeutic agent comprises a recombinant mRNA encoding a member of the SPINK protein family, or a recombinant mRNA encoding a SPINK family member polypeptide.

In embodiments, the methods further comprise subjecting the patient to a dietary modification to eliminate one or more potential food allergens.

In embodiments, the subject is human.

BRIEF DESCRIPTION OF THE DRAWINGS

FIG. 5A shows GO analysis of the SPINK7-EoE overlap gene set depicting human phenotypes.

FIG. 6A shows Hematoxylin and eosin (H&E)-stained sections of NSC or SPINK7-depleted EPC2 cells and primary esophageal epithelial cells following ALI differentiation (day 14). Arrows point on the non-cellular associated areas that were formed. FIG. 6B shows H&E-stained sections of NSC or SPINK7-depleted EPC2 cells grown for 7, 9 or 11-14 days in the ALI cultures. The percent of non-cell associate areas in the tissues is represented. Arrow point on the blabbing of the stratified layers at day 11-14. FIG. 6C shows Electron microscopy images of NSC or SPINK7-depleted EPC2 cells following ALI differentiation (day 14). Arrows depict microplicae at the epithelial junctions. Dashed arrows depict absent of microplicae at epithelial junctions.

FIG. 9A is a heat map of cytokine and chemokine expression derived from supernatants of NSC or SPINK7-depleted EPC2 cells following ALI differentiation (day 14) that were altered (All the indicated cytokines and chemokines were expressed at a concentration >1 pg/ml, -2>Fold Change (FC)>2, $P<0.05$). Data presented as the mean fold change (FC) of three independent experiments performed in duplicate and triplicate. *CXCL1/2/3—detection of CXCL1, CXCL2 and CXCL3 together. FIG. 9B is a bar graph showing IL-8 protein expression in supernatants of either NSC or SPINK7-depleted EPC2 cells that were treated either with a vehicle or with cyclosporine A (CsA), or FK506 during ALI differentiation. FIG. 9C is a bar graph showing eosinophils derived from human peripheral blood were subjected to migration assay using a transwell chamber with 5 µm pore size. KSFM media was placed at the bottom chamber and was either fresh KSFM media with or without eotaxin-1 or KSFM media derived from supernatants of differentiated EPC2 cells that were either transduced with NSC or SPINK7 shRNA.

FIG. 10A is a bar graph showing quantification of uPA activity in supernatants derived from (NSC) or SPINK7-depleted EPC2 cells following during ALI differentiation (day 7-9). FIG. 10B is a bar graph showing quantification of the activity of serine proteinases with trypsin-like activity in supernatants derived from (NSC) or SPINK7-depleted EPC2 cells and primary esophageal cells following ALI differentiation. Proteinase activity in the supernatants is calculated as nM concentrations according to standard dilutions of recombinant hKLK5. In vitro activity assays of KLK5 (FIG. 10C), KLK7 (FIG. 10D) and KLK11 (FIG. 10E) in the presence of the indicated concentrations of SPINK7. Data are represented as the mean±s.e.m.

FIG. 11A shows quantitative analysis of cells demonstrating alterations of junctional proteins from the total number of cells from NSC or SPINK7-depleted EPC2 cells following ALI differentiation. FIG. 11B shows a graph depicting FITC-dextran flux measured at day 14 of ALI differentiation from NSC and SPINK7-depleted EPC2 cells for the indicated time points. All data are representative of at least three experiments performed in triplicate and are represented as the mean±SD.

FIG. 12A is a bar graph showing FPKM values of uPA in the esophagus of EoE patients and controls. FIG. 12B is a bar graph showing analysis of the uPA proteolytic activity (active units—AU) in esophageal biopsies from 6 normal and 6 EoE patients. FIG. 12C shows expression of uPAR (according to the mean fluorescence intensity-MFI) on the cell surface of eosinophils ($7AAD^{low}$, $CD45^+$, $CD11B^+$, Siglec 8) derived from blood or esophageal biopsies from 8 EoE patients using flow cytometry. FIG. 12D is a bar graph showing quantification of trypsin-like activity in supernatants derived from NSC or SPINK7-depleted EPC2 cells that were treated with A1AT or a vehicle following ALI differentiation. FIG. 12E are electrical resistance measurements of NSC or SPINK7-depleted EPC2 cells that were treated with A1AT or a vehicle during ALI differentiation (Day 7). FIG. 12F are H&E staining images of NSC or SPINK7-depleted EPC2 cells that were treated with A1AT or a vehicle after ALI differentiation (Day 14)-add. FIG. 12G are images of co-immunofluorescence staining of E-cadherin and Filaggrin of NSC or SPINK7-depleted EPC2 cells that were treated with A1AT or a vehicle following ALI differentiation.

FIG. 14A is a structure of 3-(3-chlorophenyl) carboxy-7-hydroxymethyl coumarin. FIG. 14B is a dose response curve for 3-(3-chlorophenyl)carboxy-7-hydroxymethyl coumarin. FIG. 14C is a structure of 3-carboxy-7-hydroxymethyl coumarin. FIG. 14D is a dose response curve for 3-carboxy-7-hydroxymethyl coumarin.

DETAILED DESCRIPTION OF THE INVENTION

Figure 1:
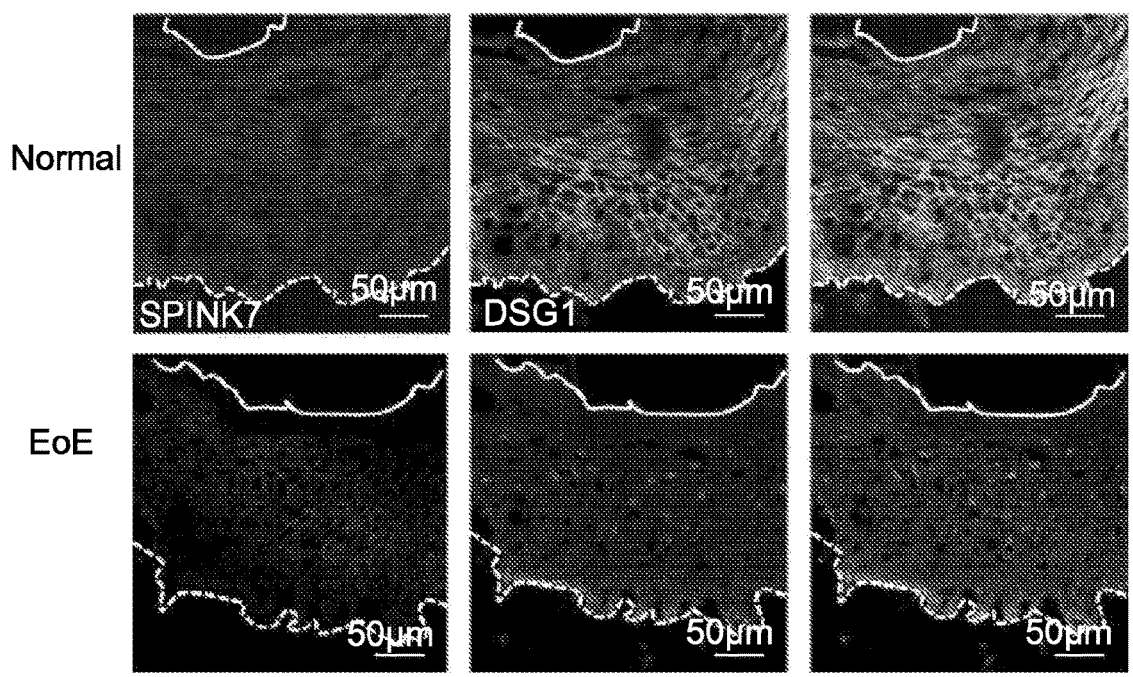
FIG. 1 shows immunofluorescence staining images of esophageal biopsy sections for DSG1 and SPINK7 with DAPI-stained nuclei; representative images of control patients (Normal) and patients with EoE (EoE) are shown. A solid line separates the lumen from the epithelium, and a dashed line separates the epithelium from the lamina propria.

The methods described here are based, in part, on the identification of the serine proteinase inhibitor kazal-type 7 (SPINK7) as a key anti-inflammatory regulator which is lost in allergic inflammation of the squamous epithelium, for example as occurs in the esophageal tissue of patients suffering from EoE. EoE is historically defined as esophageal eosinophilia (EE) that does not respond to proton pump inhibitor (PPI) therapy. It is now apparent, however, that EoE overlaps with PPI-Responsive EE, such that both disease entities are now considered the same basic process (see, e.g., Proton pump inhibitor-responsive oesophageal eosinophilia: an entity challenging current diagnostic criteria for eosinophilic oesophagitis, Molina-Infante J et al., PPI-REE Task Force of the European Society of Eosinophilic Oesophagitis (EUREOS). Gut. 2016 March; 65(3):524-31).

EoE can also be considered proteotypic for conditions characterized by inflammation of the squamous epithelium, particularly allergic inflammation. Also discovered by the present inventors is that the key molecular targets of SPINK7 include the proteinases urokinase type plasminogen activator (uPA) and kallikrein 5 (KLK5). The term "proteinase" is synonymous with the term "protease" and both terms refer to a proteolytic enzyme that acts on proteins and polypeptides by hydrolysis of peptide bonds.

The results described infra demonstrate that the loss of SPINK7 hampers esophageal barrier formation and promotes pro-inflammatory changes in epithelial cells. These pro-inflammatory changes are mediated by the uncontrolled proteolytic activity of uPA and KLK5, which are normally repressed by SPINK7. The resulting changes in the epithelial cells cause aberrant epithelial cell differentiation and impaired barrier function. These changes enable immune cells to encounter luminal antigens and promote a Th2 response. This provides the rationale for pharmacological targeting of uPA and KLK5 for the treatment of EoE, since inhibiting the proteolytic activity of these proteins would at least partially restore a key function of SPINK7 that is lost in the disease state, the downregulation of these proteinases. The data provided here further demonstrate that protein replacement with an alpha-1 anti-trypsin (A1AT) proteinase inhibitor restored some responses associated with loss of SPINK7 in vitro. This data supports the therapeutic potential of the methods described herein.

Thus, the methods described herein aim to reestablish SPINK7 checkpoint control in the squamous epithelium of a target tissue where that control has been lost or diminished, e.g., in tissues characterized by inflammation of the squamous epithelium, especially allergic inflammation. SPINK7 checkpoint control may be reestablished according to the present methods, for example, by increasing SPINK7 anti-proteinase activity directly, e.g., by replenishing SPINK7 protein in the target tissue, or indirectly, e.g., by introducing one or more serine proteinase inhibitors to the target tissue.

In embodiments, the methods described here may comprise introducing SPINK7 protein to a target tissue, for example by administering a recombinant polynucleotide encoding a SPINK7 protein, or by introducing a recombinant SPINK7 polypeptide. The methods may also comprise increasing the expression of endogenous SPINK7 in the target tissue.

In embodiments, the methods described here may also comprise administering one or more therapeutic agents that are proteinase inhibitors. In embodiments, the proteinase inhibitor is a serine proteinase inhibitor. In embodiments, the serine proteinase inhibitor is an inhibitor of an alpha-1 proteinase, a trypsin-like serine proteinase, a urokinase-type serine proteinase, or an inhibitor of uPA or KLK5, or any combination of the foregoing. In accordance with any of the foregoing embodiments, the therapeutic agent may be a small organic molecule, a polypeptide, or a nucleic acid. In embodiments, the small organic molecule is selected from the group consisting of the KLK5 inhibitors 3-(3-chlorophenyl)carboxy-7-hydroxymethyl courmarin and 3-carboxy-7-hydroxymethyl coumarin. In embodiments, the polypeptide is selected from the group consisting of an Fc fusion protein and an inhibitory antibody, e.g., targeted against uPA or KLK5, or both. In embodiments, the nucleic acid is selected from the group consisting of an anti-sense polynucleotide and an inhibitory RNA such as an miRNA or shRNA, e.g., targeted against uPA or KLK5, or both.

In embodiments, the therapeutic agent is an anti-KLK5-based therapeutic agent. In embodiments, the anti-KLK5 agent is a KLK5-Fc fusion protein, an KLK5 anti-sense polynucleotide, an KLK5-directed miRNA, an KLK5-directed shRNA, or a KLK5-directed antibody. In embodiments, the anti-KLK5-based therapeutic agent is a serine proteinase inhibitor. In embodiments, the anti-KLK5 agent is selected from 3-(3-chlorophenyl)carboxy-7-hydroxymethyl courmarin and 3-carboxy-7-hydroxymethyl coumarin.

In embodiments, the therapeutic agent may also include at least one of a compound or composition that suppresses uPA or KLK5 proteinase activity. In some embodiments, the compound or composition that suppresses uPA or KLK5 proteinase activity includes a proteinase inhibitor, an NTRK1-Fc fusion protein (neurotrophic receptor kinase 1), an NTRK1 anti-sense polynucleotide, an NTRK1-directed miRNA, an NTRK1-directed shRNA, or an NTRK1-directed antibody, including a humanized antibody.

In embodiments, uPA or KLK5 activity is suppressed by inhibiting uPA or KLK5 gene expression, inhibiting uPA or KLK5 protein expression, or inhibiting uPA or KLK5 proteinase activity, or any combination thereof. For example uPA or KLK5 proteinase activity may be inhibited directly, by an agent that inhibits the proteinase function of the protein, or indirectly, for example, by inhibiting gene or protein expression, thereby reducing the amount of uPA or KLK5 protein in the target tissue and thereby indirectly inhibiting uPA or KLK5 proteinase activity in the target tissue.

In embodiments, the therapeutic agent is a proteinase inhibitor. In embodiments, the therapeutic agent is a serine proteinase inhibitor. In embodiments, the therapeutic agent is an alpha-1 proteinase inhibitor. In embodiments, the alpha-1 proteinase inhibitor is a recombinant protein. In embodiments, the alpha-1 proteinase inhibitor is selected from PROLASTIN-C™, ZEMAIRA™, and ARALAST™.

In embodiments, the one or more therapeutic agents may be administered in the form of a pharmaceutical composition. The pharmaceutical composition may in any suitable form, as described in more detail infra.

In embodiments, the pharmaceutical composition is administered to the subject by any suitable route of administration. For example, the composition may be administered intravenously, intradermally, subcutaneously, or perorally. In embodiments, the pharmaceutical composition is administered to the subject by inhalation.

Methods of Treatment

The present disclosure provides methods for the treatment of an allergic inflammatory condition in a subject in need thereof, the allergic inflammatory condition characterized by inflammation of a squamous epithelium in a target tissue of the subject. In embodiments, the allergic inflammatory condition is EE or EoE. As discussed above the methods generally comprise increasing SPINK7 anti-proteinase activity either directly, e.g., by replenishing SPINK7 protein in the target tissue, or indirectly, e.g., by introducing one or more serine proteinase inhibitors to the target tissue.

In embodiments, an effective amount of a therapeutic agent is administered to the subject in need of treatment. In embodiments, the effective amount is a therapeutically effective amount. In embodiments, the effective amount is the amount effective to ameliorate one or more symptoms of an allergic inflammatory condition of the squamous epithelium. In embodiments, the effective amount is the amount effective to ameliorate one or more symptoms of EE or EoE. In embodiments, the effective amount is the amount effective to suppress KLK5 proteinase activity in a target tissue. In embodiments, the target tissue is esophageal tissue.

Also envisioned are methods comprising combination therapy for the treatment of an allergic inflammatory condition in a subject in need of such treatment. As used herein, "combination therapy" or "co-therapy" includes the administration of an effective amount of a primary therapeutic agent as described herein as part of a specific treatment regimen intended to provide the beneficial effect from the co-action of the primary therapeutic agent and an additional active agent, e.g., an additional active pharmaceutical ingredient (API). The beneficial effect of the combination includes, but is not limited to, pharmacokinetic or pharmacodynamic co-action resulting from the combination of therapeutic compounds. The beneficial effect of the combination may also relate to the mitigation of a toxicity, side effect, or adverse event associated with another agent in the combination. "Combination therapy" is not intended to encompass the administration of two or more of these therapeutic compounds as part of separate monotherapy regimens that incidentally and arbitrarily result in a beneficial effect that was not intended or predicted.

The at least one additional active agent may be a therapeutic agent, for example an anti-inflammatory agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to nontherapeutic agents, the beneficial effect of the combination may relate to the mitigation of a toxicity, side effect, or adverse event associated with a therapeutically active agent in the combination.

Thus, in embodiments, the methods described here may further comprise administering to the subject at least one additional active agent. In embodiments, the at least one additional active agent is an anti-inflammatory agent. In embodiments, the at least one additional active agent is an IL-13 inhibitor, a non-steroidal anti-inflammatory drug (NSAID), a cytokine inhibitor, or a steroid. In embodiments, the at least one additional active agent is a proton pump inhibitor.

In the context of combination therapy, the administration of the primary therapeutic agent, may be simultaneous with or sequential to the administration of the one or more additional active agents. In another embodiment, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a primary therapeutic agent as described herein.

The one or more additional active agents can be formulated for co-administration with the primary therapeutic agent in a single dosage form. The one or more additional active agents can be administered separately from the dosage form that comprises the primary therapeutic agent. When the additional active agent is administered separately from the primary therapeutic agent, it can be by the same or a different route of administration as the primary therapeutic agent.

Preferably, the administration of a composition comprising the primary therapeutic agent in combination with one or more additional active agents provides a synergistic response in the subject being treated. In this context, the term "synergistic" refers to the efficacy of the combination being more effective than the additive effects of either single therapy alone. The synergistic effect of a combination therapy according to the disclosure can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of the compounds of the present disclosure in further combination with non-drug therapies (e.g., diet modification). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In embodiments, the amount of the therapeutic agent administered to the subject is a therapeutically effective amount. The term "therapeutically effective amount" refers to an amount sufficient to treat, ameliorate a symptom of, reduce the severity of, or reduce the duration of the disease or disorder being treated or enhance or improve the therapeutic effect of another therapy, or sufficient to exhibit a detectable therapeutic effect in the subject.

An effective amount of the therapeutic agent can be administered once or twice daily, from two to five times daily, up to two times or up to three times daily, or up to eight times daily.

In accordance with the methods described herein, a "subject in need thereof" is a subject having an allergic inflammatory condition characterized by inflammation of the squamous epithelium in a target tissue. In specific embodiments, the subject is a subject having EE or EoE.

A "subject" includes a mammal. The mammal can be any mammal, for example, a human, primate, vertebrate, bird, mouse, rat, fowl, dog, cat, cow, horse, goat, camel, sheep or a pig. Preferably, the subject is a human. The term "patient" refers to a human subject.

The present disclosure also provides a monotherapy for the treatment of EoE. As used herein, "monotherapy" refers to the administration of a single active or therapeutic compound, e.g., a proteinase inhibitor or an anti-KLK5-based therapeutic agent, to a subject in need thereof.

As used herein, "treatment", "treating" or "treat" describes the management and care of a patient for the purpose of combating a disease, condition, or disorder and includes the administration of a proteinase inhibitor or an anti-KLK5-based therapeutic agent to alleviate the symptoms or complications of the allergic inflammatory disease, disorder, or condition.

As used herein, "prevention", "preventing" or "prevent" describes reducing or eliminating the onset of the symptoms or complications of the allergic inflammatory disease, disorder, or condition and includes the administration of a proteinase inhibitor or an anti-KLK5-based therapeutic agent to reduce the onset, development or recurrence of symptoms of the disease, disorder, or condition.

In one embodiment, the administration of a proteinase inhibitor or an anti-KLK5-based therapeutic agent leads to the elimination of a symptom or complication of the disease or condition being treated, however elimination of the disease, disorder, or condition is not required. In one embodiment, the severity of the symptom is decreased.

Pharmaceutical Compositions and Formulations

The present disclosure provides pharmaceutical compositions comprising an amount of a therapeutic agent as described supra. For example, the therapeutic agent may comprise a recombinant polynucleotide encoding a SPINK7 protein, a recombinant SPINK7 polypeptide, or another agent effective to increase the expression and/or amount of endogenous SPINK7 mRNA and/or protein in the target tissue. The therapeutic agent may also be proteinase inhibitor and/or a specific inhibitor of uPA and/or KLK5.

In embodiments, the proteinase inhibitor, anti-uPA or anti-KLK5 based therapeutic agent is combined with at least one additional active agent in a single dosage form. In embodiments, the at least one additional active agent is selected from an anti-inflammatory agent selected from an IL-13 inhibitor, a non-steroidal anti-inflammatory drug (NSAID), a steroid, and a cytokine inhibitor, a PPI inhibitor, and combinations thereof.

A "pharmaceutical composition" is a formulation containing the therapeutic agent in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient subject or patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in m2, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the disclosure may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition may be in a form suitable for administration by inhalation, for example as an aqueous or non-aqueous aerosol, or as a dry powder. In embodiments, the pharmaceutical composition is an aqueous solution adapted for delivery via a nebulizer, including jet, vibrating mesh, and static mesh or orifice nebulizers. In embodiments, the pharmaceutical composition is a dry powder adapted for delivery via a dry powder inhaler device.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present disclosure with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present disclosure may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present disclosure together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present disclosure may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present disclosure as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present disclosure can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the disclosure are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present disclosure also provides packaging and kits comprising pharmaceutical compositions for use in the methods of the present disclosure. The kit can comprise one or more containers selected from the group consisting of a bottle, a vial, an ampoule, a blister pack, and a syringe. The kit can further include one or more of instructions for use in treating and/or preventing a disease, condition or disorder of the present disclosure, one or more syringes, one or more applicators, or a sterile solution suitable for reconstituting a pharmaceutical composition of the present disclosure.

All percentages and ratios used herein, unless otherwise indicated, are by weight. Other features and advantages of the present disclosure are apparent from the different examples. The provided examples illustrate different components and methodology useful in practicing the present disclosure. The examples do not limit the claimed disclosure. Based on the present disclosure the skilled artisan can identify and employ other components and methodology useful for practicing the present disclosure.

EXAMPLES

The following non-limiting examples are provided to further illustrate embodiments of the invention disclosed herein. It will be appreciated by those of skill in the art that the techniques disclosed in the examples that follow represent approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

SUMMARY

As described more fully below, we show that the serine peptidase inhibitor kazal-type 7 (SPINK7) is an important anti-inflammatory check in the esophageal epithelium and is markedly down-regulated in eosinophilic esophagitis (EoE), an inflammatory TH2 type immune disease of the esophagus, while being expressed at relatively high levels in normal esophageal epithelium. We further show that loss of SPINK7 results in an epithelial cell differentiation defect, reduced barrier protein expression, impaired barrier function, and pro-inflammatory cytokine production. Protein replacement with an alpha-1 anti-trypsin proteinase inhibitor restored some responses associated with loss of SPINK7 in vitro. Our data show that the endogenous balance between SPINK7 and its target proteinases (uPA and KLK5) is a key checkpoint in regulating mucosal differentiation, barrier function and Th2-associated responses. Moreover, our data suggest that protein replacement with proteinase inhibitors holds therapeutic promise.

To investigate the role of SPINK7 in EoE, an in vitro system of human esophageal epithelial cells that were subjected to air-liquid interface (ALI) to induce squamous cell differentiation was used. Cells were stably transduced with either non-silencing control or SPINK7 shRNAs. The integrity of the epithelium was examined by barrier function assays complemented by histological and ultrastructural analyses and immune-fluorescence of junctional proteins. Proteinase activity, transcriptional alterations and identification SPINK7's downstream targets were also assessed. Cytokine and chemokine secretion was analyzed after SPINK7 gene silencing. The results demonstrated that SPINK7 was a key anti-inflammatory checkpoint in the esophageal epithelium.

The results showed that depletion of SPINK7 in esophageal epithelial cells induced architectural changes in esophageal epithelial cells reminiscent of those observed in patients with EoE including acantholysis and epithelial cleft formation, as well as impaired barrier function. The loss of SPINK7 also increased trypsin-like (>2 fold increase; P=0.004) and urokinase-type plasminogen activator (uPA) activity (2-fold, P=006). In vitro, SPINK7 inhibited the serine proteinase—kallikrein (KLK)5, but not KLK7 nor KLK11.

KLK5 is known to be involved in the regulation of the skin barrier. Furthermore, loss of SPINK7 was sufficient for induction of architectural alterations in junctional complexes, loss of ultrastructural zipper-like intercellular junctions, delocalization of the junctional proteins E-cadherin, β-catenin and desmoglein-1, decreased expression of the barrier protein filaggrin, as well as impaired barrier function.

In addition, SPINK7-depleted epithelial cells over-expressed a unique set of cytokines and chemokines that promote immune responses. Loss of SPINK7 unleashed the production of a series of pro-inflammatory cytokines and chemokines including TSLP, GM-CSF, TNFα, and IL-8. RNA sequencing substantiated that loss of SPINK7 was an upstream event in eliciting innate immune responses and cellular changes characteristic of inflammatory diseases of the epithelium.

Finally, a genetic interaction between SPINK7, TSLP and PLAU in EoE patients was identified, further linking SPINK7 to allergic responses. Epistasis between genetic variants in the SPINK, TSLP and PLAU loci were shown to contribute to EoE susceptibility. Susceptibility for EoE was impacted by epistasis between genetic variants in SPINK7 and PLAU (gene product uPA) with atopy risk variants in ST2 and TSLP.

Collectively, the data demonstrate that deficiency of SPINK7 in epithelial cells induces a profound pro-inflammatory state characterized by impaired barrier function, defect in cellular differentiation, and cytokine production. Combined with genetic interaction between SPINK and TSLP, the endogenous balance between the natural proteinase inhibitor SPINK7 and proteinases (uPA and KLK5) is a key checkpoint in regulating mucosal Th2-associated immune responses.

Example 1: Specific SPINK7 Expression in Eosinophilic Esophagitis (EoE)

Of 8 SPINK members expressed in the esophagus; the most highly expressed were SPINK5 and SPINK7 (1450 and 831 FPKM, respectively) based on genome wide RNA sequencing data of the human esophagus (data not shown, shows the normalized FPKM values for SPINKs expression in healthy and EoE patients from RNAseq data of esophageal biopsies from 6 healthy controls (Normal), and 10 patients with active EoE) (Sherrill, J. D. et al. *Genes and immunity* 15, 361-369 (2014)). SPINK7 FPKM value was >150-fold greater than SPINK8 (5 FPKM), which was the most highly expressed SPINK besides SPINK5 and SPINK7. Four of the 8 expressed SPINKs were decreased in EoE with SPINK7 showing the most statistically significant downregulation (16-fold reduction; $p=3\times10^{-8}$) compared to control (data not shown).

Analysis of esophageal biopsies (n=133 patients) demonstrated that SPINK7 mRNA was down regulated in EoE compared to controls (data not shown) (Wen, T. et al. *Gastroenterology* 145, 1289-1299 (2013)). Microarray data of esophageal biopsies from 14 healthy controls (Normal), 22 patients with inactive or 19 patients with active EoE was also performed (data not shown). This was further validated by quantitative PCR (data not shown).

Confocal microscopy revealed SPINK7 expression throughout all epithelial layers with the highest expression in the suprabasal epithelium and its expression was significantly down-regulated together with DSG1 in EoE patients compared to control individuals (FIG. 1). There was a positive correlation between SPINK7 and epithelial products including differentiation and adhesion molecules and a negative correlation between SPINK7 and cytokines such as IL-5 and CCL26 (data not shown), demonstrating that the loss of SPINK7 might regulate epithelial integrity and promote increased inflammatory response.

Figure 2:
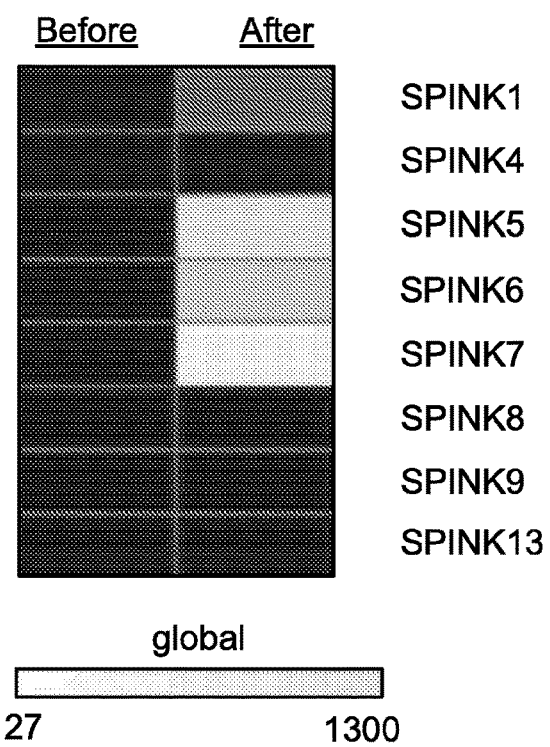
FIG. 2 shows a heat map of SPINKs expression before differentiation of EPC2 cells (day 0) or after 14 days of ALI differentiation.

Example 2: SPINK Expression is Part of the Epithelial Differentiation Program Epithelial differentiation was induced by culture of either an esophageal epithelial progenitor cell line (EPC2) or primary esophageal epithelial cells exposed to the air-liquid interface (ALI), as reported (Sherrill, J. D. et al. *Mucosal immunology* 7, 718-729 (2014), Kalabis, J. et al. *Nature protocols* 7, 235-246 (2012), and Frankart, A. et al. *Experimental dermatology* 21, 871-875 (2012)). Under these conditions, the expression of SPINK5 and SPINK7 increased by 915-fold and 752-fold, respectively (p=0.0007, p<$10^{-10}$, respectively). SPINK5 and SPINK7 were the most highly expressed SPINK family members following epithelial cell differentiation in vitro (FIG. 2), consistent with the in vivo expression pattern.

Example 3: Loss of SPINK7 Impairs Epithelial Differentiation

SPINK7 expression was silenced specifically by shRNAi targeting a region of SPINK7 that exhibited relatively less conservation with SPINK5 which on average exhibits 51% identity to SPINK7 (data not shown). EPC2 cells and primary esophageal epithelial cells were stably transduced with vector expressing either shRNA target SPINK7 or non-silencing control (NSC) shRNA. In cells expressing the SPINK7-directed shRNA, near complete loss of SPINK7 expression was observed with no effect on SPINK5, indicating specificity of the gene silencing construct (data not shown).

Whole transcriptome sequencing analysis was performed on EPC2 cells after ALI differentiation (data not shown). This analysis revealed 270 genes that were differentially expressed in the SPINK7-deficient cells compared to NSC cells (p<0.05, fold change>2, RPKM>1) (Table 1, below). The modified genes were enriched for those involved in epidermal differentiation and inflammation including the transcription factors STAT1 and NFATC2 and cytokines such as IL23, IL37, and CCL24 and included decreased expression of FLG, FLG2, LOR, keratins, tranglutaminases and interleukin 36 receptor antagonist (IL36RN) (data not shown and Table 1). Functionally it was predicted that loss of SPINK7 regulated innate immune responses and interferon regulatory factors (data not shown).

TABLE 1

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| AADACL2 | 8.660 | 0.353 | 0.041 | 3.12E-10 |
| ABCG4 | 1.252 | 0.292 | 0.233 | 0.001276785 |
| ABHD12B | 1.025 | 0.217 | 0.212 | 0.000227346 |
| ABP1 | 6.362 | 0.491 | 0.077 | 2.62E-08 |
| ACER1 | 10.451 | 1.513 | 0.145 | 5.26E-13 |
| ACP5 | 3.783 | 1.509 | 0.399 | 0.000721352 |
| ACPP | 9.356 | 3.554 | 0.380 | 2.79E-06 |
| ALDH1A3 | 200.888 | 675.867 | 3.364 | 1.95E-10 |
| ALDH5A1 | 1.778 | 0.651 | 0.366 | 0.000678249 |
| ALOX12B | 17.886 | 5.411 | 0.303 | 7.18E-05 |
| ANKRD35 | 8.693 | 2.993 | 0.344 | 8.95E-06 |
| APOE | 22.695 | 5.167 | 0.228 | 0.001409301 |
| AQP3 | 70.172 | 34.698 | 0.494 | 0.000320651 |
| ARL4A | 10.506 | 3.386 | 0.322 | 0.000103552 |
| ASAP3 | 7.982 | 2.973 | 0.372 | 1.37E-07 |
| ASPG | 3.398 | 0.462 | 0.136 | 0.000822682 |
| ASPRV1 | 22.411 | 0.570 | 0.025 | 9.80E-29 |
| BCAS1 | 6.504 | 0.615 | 0.095 | 9.62E-05 |
| BGN | 0.535 | 1.463 | 2.735 | 0.004746858 |
| BNIPL | 27.186 | 12.137 | 0.446 | 0.000101291 |
| BST2 | 4.337 | 46.397 | 10.697 | 2.01E-21 |
| C10orf10 | 2.086 | 3.710 | 1.779 | 5.88E-05 |
| C10orf99 | 89.123 | 23.786 | 0.267 | 3.08E-09 |
| C17orf109 | 1.834 | 0.297 | 0.162 | 0.000325599 |
| C19orf66 | 5.604 | 16.880 | 3.012 | 0.001476392 |
| C1orf68 | 3.792 | 0.177 | 0.047 | 1.67E-14 |
| C2orf54 | 12.718 | 2.398 | 0.189 | 8.82E-06 |
| C5orf46 | 17.411 | 2.016 | 0.116 | 5.67E-07 |
| C6orf15 | 22.207 | 6.762 | 0.305 | 4.70E-11 |
| CA13 | 1.737 | 0.749 | 0.431 | 0.001446637 |
| CALB2 | 10.486 | 4.100 | 0.391 | 0.00031438 |
| CALML5 | 49.497 | 4.000 | 0.081 | 6.89E-15 |
| CAMK1D | 1.690 | 0.582 | 0.344 | 0.001481232 |
| CASP14 | 11.974 | 0.941 | 0.079 | 8.46E-31 |
| CCL24 | 3.902 | 0.074 | 0.019 | 1.27E-05 |
| CDH26 | 1.359 | 0.337 | 0.248 | 3.76E-05 |
| CEACAM5 | 24.091 | 2.054 | 0.085 | 1.62E-14 |
| CEACAM7 | 10.835 | 0.495 | 0.046 | 3.64E-05 |
| CERCAM | 3.872 | 8.326 | 2.150 | 0.000384542 |
| CERS4 | 20.319 | 8.394 | 0.413 | 0.000100833 |
| CHRNB1 | 2.566 | 6.303 | 2.457 | 0.000303905 |
| CLCA4 | 35.921 | 3.034 | 0.084 | 0.003852654 |
| CLDN17 | 108.849 | 49.550 | 0.455 | 0.005591202 |
| CLDN4 | 35.014 | 71.975 | 2.056 | 0.000880654 |
| CMPK2 | 3.097 | 18.705 | 6.039 | 1.21E-06 |
| CMTM8 | 2.033 | 0.754 | 0.371 | 0.002603997 |
| CORO6 | 0.597 | 1.792 | 3.000 | 0.000206577 |
| CPPED1 | 5.802 | 1.148 | 0.198 | 2.67E-12 |
| CRISP3 | 12.852 | 0.217 | 0.017 | 0.000162726 |
| CSF2RB | 1.931 | 0.592 | 0.306 | 0.003264803 |
| CSGALNACT1 | 5.004 | 2.257 | 0.451 | 0.000148176 |
| CXCL14 | 106.453 | 52.935 | 0.497 | 2.68E-06 |
| CXCL17 | 12.814 | 1.546 | 0.121 | 0.000343615 |
| CXCR2 | 2.104 | 0.796 | 0.378 | 0.001546073 |
| CYP2C18 | 15.091 | 6.752 | 0.447 | 1.79E-05 |
| CYP4B1 | 10.572 | 0.701 | 0.066 | 2.85E-15 |
| CYP4F11 | 0.253 | 1.372 | 5.423 | 9.65E-05 |
| CYP4F22 | 6.983 | 1.593 | 0.228 | 3.91E-07 |
| DACT2 | 0.164 | 1.356 | 8.269 | 1.16E-08 |
| DAPL1 | 9.630 | 1.303 | 0.135 | 1.23E-07 |
| DDX58 | 8.009 | 31.227 | 3.899 | 0.00063373 |
| DDX60L | 5.122 | 21.791 | 4.254 | 3.76E-05 |
| DGAT2 | 26.942 | 8.160 | 0.303 | 9.38E-07 |
| DHX58 | 1.742 | 4.709 | 2.704 | 0.002056853 |
| DIO2 | 8.295 | 0.638 | 0.077 | 1.31E-05 |
| DSC1 | 19.955 | 0.412 | 0.021 | 1.16E-88 |
| DSG1 | 196.343 | 36.276 | 0.185 | 1.40E-20 |
| DTX3L | 6.590 | 22.720 | 3.448 | 0.000215309 |
| EIF2AK2 | 9.327 | 29.432 | 3.155 | 0.00059743 |
| ENTPD2 | 1.248 | 3.743 | 3.000 | 0.000431713 |
| EPHA4 | 8.987 | 2.517 | 0.280 | 4.79E-10 |
| EPHB6 | 1.121 | 0.401 | 0.358 | 0.000982833 |
| EPHX1 | 10.980 | 4.997 | 0.455 | 0.000148811 |
| EPS8 | 1.132 | 4.527 | 3.998 | 0.001324941 |

TABLE 1-continued

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| EPSTI1 | 2.301 | 14.709 | 6.391 | 1.49E-06 |
| ERP27 | 2.173 | 0.475 | 0.219 | 8.93E-05 |
| FABP5 | 474.430 | 213.745 | 0.451 | 1.09E-05 |
| FAM3D | 28.282 | 2.147 | 0.076 | 2.78E-06 |
| FAM40B | 2.439 | 5.374 | 2.204 | 0.002121605 |
| FAM83C | 1.187 | 0.268 | 0.226 | 2.81E-05 |
| FCRLA | 0.313 | 1.057 | 3.375 | 0.004394847 |
| FETUB | 10.757 | 0.296 | 0.028 | 8.13E-14 |
| FLG | 16.017 | 1.814 | 0.113 | 1.33E-32 |
| FLG2 | 33.534 | 0.625 | 0.019 | 1.14E-58 |
| FLVCR2 | 11.514 | 4.513 | 0.392 | 7.86E-08 |
| FUOM | 3.130 | 0.919 | 0.294 | 0.007959923 |
| GBP1 | 6.595 | 15.532 | 2.355 | 0.00358778 |
| GCNT3 | 33.422 | 8.056 | 0.241 | 0.000598123 |
| GJB6 | 128.769 | 53.132 | 0.413 | 2.39E-06 |
| GLA | 28.411 | 11.992 | 0.422 | 0.000244569 |
| GPLD1 | 2.115 | 0.512 | 0.242 | 1.10E-05 |
| GPR111 | 1.087 | 0.359 | 0.330 | 7.52E-05 |
| GPRIN2 | 1.144 | 0.165 | 0.144 | 0.000662353 |
| GSTA4 | 16.732 | 6.224 | 0.372 | 2.12E-05 |
| GUCY1A3 | 4.661 | 1.665 | 0.357 | 0.000244799 |
| HAL | 2.715 | 0.163 | 0.060 | 3.72E-29 |
| HERC5 | 1.420 | 4.324 | 3.045 | 0.003040819 |
| HERC6 | 6.827 | 31.523 | 4.618 | 5.00E-06 |
| HEXA | 14.359 | 3.140 | 0.219 | 1.67E-08 |
| HLA-A | 64.534 | 156.953 | 2.432 | 1.12E-06 |
| HLA-B | 77.075 | 217.200 | 2.818 | 5.00E-06 |
| HLA-C | 44.366 | 105.895 | 2.387 | 2.37E-05 |
| HLA-F | 6.775 | 19.874 | 2.934 | 1.88E-05 |
| HOPX | 1132.244 | 344.550 | 0.304 | 0.000505595 |
| HPGD | 40.814 | 11.103 | 0.272 | 0.008896222 |
| HS3ST6 | 5.377 | 1.160 | 0.216 | 5.44E-05 |
| HYAL4 | 2.019 | 0.523 | 0.259 | 0.000599287 |
| IFI27 | 172.272 | 556.810 | 3.232 | 1.09E-07 |
| IFI35 | 5.633 | 25.363 | 4.502 | 2.46E-05 |
| IFI44 | 19.200 | 90.249 | 4.700 | 2.05E-06 |
| IFI44L | 1.920 | 25.357 | 13.210 | 1.68E-10 |
| IFI6 | 66.483 | 434.423 | 6.534 | 4.58E-12 |
| IFIH1 | 9.872 | 33.182 | 3.361 | 6.38E-06 |
| IFIT1 | 26.543 | 231.184 | 8.710 | 8.67E-07 |
| IFIT2 | 2.513 | 10.464 | 4.164 | 0.000772178 |
| IFIT3 | 13.555 | 85.022 | 6.272 | 8.89E-06 |
| IFIT5 | 5.205 | 16.352 | 3.142 | 9.23E-06 |
| IFITM1 | 42.317 | 156.612 | 3.701 | 1.08E-07 |
| IFITM3 | 127.955 | 312.570 | 2.443 | 7.41E-06 |
| IFNK | 0.570 | 10.002 | 17.540 | 7.94E-10 |
| IGFBP2 | 11.995 | 4.819 | 0.402 | 0.000117061 |
| IGFL2 | 171.138 | 49.653 | 0.290 | 3.37E-08 |
| IGFL3 | 14.557 | 7.769 | 0.534 | 0.001665316 |
| IL1F10 | 3.103 | 0.894 | 0.288 | 0.001679465 |
| IL23A | 13.831 | 3.996 | 0.289 | 0.002157056 |
| IL36B | 2.940 | 0.640 | 0.218 | 8.71E-05 |
| IL36RN | 51.959 | 10.819 | 0.208 | 1.28E-07 |
| IL37 | 1.898 | 0.271 | 0.143 | 0.002081829 |
| IRF7 | 5.425 | 21.631 | 3.987 | 1.82E-05 |
| ISG15 | 60.183 | 239.167 | 3.974 | 6.01E-05 |
| KLK1 | 1.831 | 0.489 | 0.267 | 0.001107183 |
| KLK12 | 46.708 | 14.034 | 0.300 | 0.001227423 |
| KLK5 | 197.057 | 480.144 | 2.437 | 9.30E-09 |
| KPRP | 31.654 | 10.894 | 0.344 | 5.07E-08 |
| KRT10 | 1006.965 | 62.168 | 0.062 | 5.27E-14 |
| KRT19 | 340.813 | 666.430 | 1.955 | 0.001106237 |
| KRT2 | 16.754 | 1.845 | 0.110 | 1.18E-07 |
| KRT23 | 195.775 | 93.248 | 0.476 | 0.00690264 |
| KRT24 | 2.346 | 3.062 | 1.306 | 7.22E-05 |
| KRT27 | 3.380 | 0.312 | 0.092 | 4.64E-09 |
| KRT4 | 460.140 | 54.598 | 0.119 | 9.88E-10 |
| KRT79 | 1.505 | 0.520 | 0.346 | 0.005201351 |
| KRTDAP | 2272.468 | 139.936 | 0.062 | 6.55E-24 |
| LAMP3 | 1.053 | 5.514 | 5.235 | 1.49E-05 |
| LCE1A | 64.188 | 17.932 | 0.279 | 1.92E-06 |
| LCE1C | 45.575 | 5.458 | 0.120 | 2.18E-13 |
| LCE1D | 23.419 | 2.908 | 0.124 | 3.98E-09 |
| LCE1E | 15.082 | 1.425 | 0.094 | 3.73E-10 |
| LCE2A | 36.115 | 8.891 | 0.246 | 1.42E-05 |
| LCE2B | 72.175 | 12.031 | 0.167 | 1.64E-11 |
| LCE2C | 71.599 | 21.581 | 0.301 | 4.29E-06 |
| LCE2D | 43.298 | 18.662 | 0.431 | 0.000129137 |
| LCP1 | 1.212 | 7.302 | 6.024 | 1.47E-05 |
| LGALS7B | 22.811 | 8.105 | 0.355 | 0.000816353 |
| LIPK | 11.476 | 3.990 | 0.348 | 7.60E-06 |
| LIPM | 20.570 | 3.419 | 0.166 | 1.29E-06 |
| LOR | 24.228 | 2.071 | 0.085 | 1.31E-19 |
| LY6D | 16.071 | 3.964 | 0.247 | 9.66E-10 |
| LY6G6C | 41.299 | 8.997 | 0.218 | 8.14E-12 |
| LYNX1 | 516.559 | 162.668 | 0.315 | 0.000447521 |
| LYPD2 | 157.658 | 30.035 | 0.191 | 0.000101254 |
| MAFB | 1.507 | 5.373 | 3.565 | 4.90E-08 |
| MAL | 67.102 | 2.602 | 0.039 | 8.47E-06 |
| MARCH3 | 1.206 | 0.578 | 0.479 | 0.000504864 |
| MFAP3L | 2.372 | 0.892 | 0.376 | 0.001286441 |
| MT1X | 441.374 | 169.262 | 0.383 | 3.19E-05 |
| MUC15 | 21.341 | 6.225 | 0.292 | 0.001802868 |
| MX1 | 31.721 | 194.408 | 6.129 | 2.22E-06 |
| MX2 | 3.081 | 39.028 | 12.667 | 1.03E-05 |
| MYH14 | 1.521 | 0.184 | 0.121 | 0.000132386 |
| MYL9 | 9.824 | 35.926 | 3.657 | 0.000205203 |
| MYZAP | 20.038 | 8.381 | 0.418 | 1.95E-05 |
| NEBL | 14.833 | 4.070 | 0.274 | 2.62E-06 |
| NFATC2 | 1.484 | 0.557 | 0.375 | 7.22E-08 |
| NLRC5 | 0.594 | 2.995 | 5.042 | 0.000136269 |
| OAS1 | 32.972 | 95.846 | 2.907 | 7.35E-05 |
| OAS2 | 26.204 | 105.856 | 4.040 | 7.77E-05 |
| OAS3 | 6.712 | 42.148 | 6.279 | 5.04E-06 |
| OASL | 5.341 | 18.148 | 3.398 | 0.00072384 |
| OPHN1 | 0.856 | 2.336 | 2.730 | 0.000195346 |
| PAQR5 | 3.609 | 1.586 | 0.439 | 3.46E-06 |
| PARP10 | 1.734 | 5.896 | 3.401 | 0.002403439 |
| PARP12 | 6.048 | 17.888 | 2.958 | 0.000653571 |
| PARP14 | 7.261 | 25.702 | 3.540 | 5.17E-06 |
| PARP9 | 18.443 | 66.115 | 3.585 | 1.37E-05 |
| PCSK6 | 3.616 | 0.475 | 0.131 | 1.84E-11 |
| PGLYRP4 | 28.278 | 11.122 | 0.393 | 0.001807447 |
| PHEX | 3.483 | 1.178 | 0.338 | 0.00188494 |
| PI3 | 20386.800 | 6606.973 | 0.324 | 6.87E-06 |
| PLA2G3 | 3.933 | 0.556 | 0.141 | 9.00E-16 |
| PLA2G4B | 7.873 | 3.766 | 0.478 | 0.000902824 |
| PLA2G4D | 1.409 | 0.187 | 0.133 | 5.02E-07 |
| PLBD1 | 78.931 | 26.987 | 0.342 | 0.001063172 |
| PLEKHA4 | 0.531 | 2.175 | 4.098 | 0.004923693 |
| PLXDC2 | 21.965 | 8.362 | 0.381 | 0.00015418 |
| POF1B | 129.287 | 58.641 | 0.454 | 0.001401452 |
| POLR2J3 | 14.311 | 3.087 | 0.216 | 0.00017694 |
| POSTN | 3.548 | 0.767 | 0.216 | 0.001041589 |
| PPAP2C | 5.745 | 1.838 | 0.320 | 0.000432425 |
| PPFIBP2 | 8.574 | 4.602 | 0.537 | 9.00E-05 |
| PPP2R2C | 4.463 | 1.860 | 0.417 | 0.000296121 |
| PRIC285 | 3.781 | 14.161 | 3.745 | 0.006690084 |
| PRSS3 | 11.472 | 2.912 | 0.254 | 1.17E-09 |
| PSAPL1 | 1.218 | 0.077 | 0.063 | 7.33E-16 |
| PSORS1C2 | 4.636 | 1.892 | 0.408 | 0.000746804 |
| PYDC1 | 5.163 | 0.582 | 0.113 | 8.50E-08 |
| RDH12 | 60.584 | 12.719 | 0.210 | 2.35E-05 |
| RGMA | 0.731 | 2.055 | 2.813 | 0.000957165 |
| RNF213 | 3.149 | 10.248 | 3.255 | 0.000151269 |
| RPTN | 152.773 | 23.960 | 0.157 | 7.91E-08 |
| RSAD2 | 14.663 | 51.466 | 3.510 | 0.000657584 |
| S100A4 | 10.952 | 1.743 | 0.159 | 0.000169518 |
| SAMD9L | 3.282 | 8.296 | 2.528 | 0.000122563 |
| SAPCD2 | 1.359 | 5.105 | 3.756 | 5.74E-06 |
| SCCPDH | 1.377 | 0.470 | 0.342 | 0.001095738 |
| SDR9C7 | 23.268 | 3.506 | 0.151 | 2.74E-14 |
| SEMA3B | 0.466 | 2.348 | 5.042 | 5.20E-08 |
| SERPINA12 | 17.941 | 0.441 | 0.025 | 1.41E-19 |
| SERPINB10 | 1.707 | 0.303 | 0.177 | 0.002079277 |
| SERPINB11 | 1.196 | 0.043 | 0.036 | 0.000254419 |
| SERPINB12 | 14.375 | 0.628 | 0.044 | 7.75E-25 |
| SERPINB4 | 2.135 | 1.017 | 0.476 | 0.003011842 |

TABLE 1-continued

Transcriptomic analysis of genes differentially expressed after SPINK7-silencing compared to control in differentiated EPC2 cells

| Gene_ID | RPKM Control | RPKM SPINK7 | Fold Change | p-value |
|---|---|---|---|---|
| SH3GL3 | 2.644 | 0.436 | 0.165 | 9.30E−05 |
| SHF | 5.075 | 1.551 | 0.306 | 0.000279762 |
| SHISA4 | 0.777 | 2.518 | 3.240 | 0.00214213 |
| SHISA9 | 1.303 | 0.520 | 0.399 | 0.002362574 |
| SIPA1L2 | 4.620 | 1.891 | 0.409 | 5.71E−08 |
| SLC10A6 | 3.110 | 1.231 | 0.396 | 0.000694286 |
| SLC15A1 | 3.903 | 0.804 | 0.206 | 6.66E−12 |
| SLC15A3 | 0.553 | 3.453 | 6.245 | 7.80E−06 |
| SLC39A2 | 15.331 | 4.958 | 0.323 | 9.55E−06 |
| SLURP1 | 395.306 | 106.847 | 0.270 | 3.63E−08 |
| SP100 | 16.667 | 45.318 | 2.719 | 0.003767804 |
| SPINK5 | 1307.389 | 256.405 | 0.196 | 2.76E−06 |
| SPINK7 | 601.815 | 48.483 | 0.081 | 1.42E−20 |
| SPRR1A | 1630.121 | 731.475 | 0.449 | 0.000117351 |
| SPRR2B | 701.221 | 368.342 | 0.525 | 0.000175788 |
| SPRY1 | 1.568 | 0.796 | 0.507 | 0.003023006 |
| SPTLC3 | 21.596 | 10.087 | 0.467 | 1.76E−07 |
| SPTSSB | 14.270 | 0.145 | 0.010 | 3.44E−12 |
| STAT1 | 40.731 | 165.908 | 4.073 | 4.60E−05 |
| SYNGR1 | 1.143 | 0.467 | 0.408 | 0.009279141 |
| SYTL2 | 2.970 | 6.445 | 2.170 | 0.000346622 |
| SYTL5 | 1.017 | 0.137 | 0.135 | 0.000953611 |
| TAGLN | 16.779 | 45.100 | 2.688 | 0.000663656 |
| TCN1 | 22.208 | 3.108 | 0.140 | 5.41E−08 |
| TEX101 | 1.478 | 0.153 | 0.104 | 0.005571691 |
| TGM2 | 1.362 | 5.369 | 3.941 | 0.001837368 |
| TGM5 | 4.919 | 0.874 | 0.178 | 1.55E−14 |
| THEM5 | 4.333 | 0.239 | 0.055 | 2.54E−11 |
| TMEM45B | 45.839 | 18.799 | 0.410 | 0.002362663 |
| TMPRSS11B | 71.841 | 5.468 | 0.076 | 0.003055064 |
| TMPRSS11D | 14.631 | 2.846 | 0.195 | 0.000188995 |
| TPRG1 | 6.638 | 2.232 | 0.336 | 9.13E−05 |
| TRANK1 | 0.742 | 3.210 | 4.324 | 0.000934694 |
| TREX2 | 1.424 | 0.410 | 0.288 | 0.000733089 |
| TRIM25 | 12.867 | 33.370 | 2.593 | 0.000104414 |
| UPK3BL | 114.888 | 21.787 | 0.190 | 7.78E−06 |
| USP18 | 1.610 | 10.015 | 6.221 | 8.46E−06 |
| VSIG8 | 22.682 | 6.366 | 0.281 | 1.91E−05 |
| WDR76 | 0.161 | 1.464 | 9.072 | 0.004154222 |
| WFDC5 | 52.581 | 22.585 | 0.430 | 0.000134007 |
| WNT9A | 0.234 | 1.039 | 4.450 | 0.00437511 |
| XAF1 | 6.888 | 31.901 | 4.632 | 2.34E−07 |
| XKRX | 6.464 | 2.415 | 0.374 | 6.86E−05 |
| ZBTB7C | 1.037 | 0.120 | 0.115 | 1.91E−06 |
| ZNF433 | 1.908 | 0.447 | 0.234 | 0.000604875 |
| ZNF556 | 4.679 | 0.794 | 0.170 | 2.88E−05 |
| ZNF626 | 1.118 | 0.363 | 0.324 | 0.001935167 |
| ZNF662 | 1.556 | 0.164 | 0.105 | 4.66E−18 |

FPKM, fold-change (FC) and p-values of genes differentially expressed after SPINK7 gene silencing as compared to NSC in EPC2 cells differentiated at ALI cultures for 14 days identified by RNA sequencing (Fold change > 2, p < 0.05, FPKM > 1).

Furthermore, genes expression of EPC2 monolayer culture (day 0 of ALI culture) and differentiated EPC2 cells in ALI culture (Day 14 of differentiation) were compared. This analysis revealed 3225 differentially expressed genes (p<0.05, fold change>2, RPKM>1) (data not shown). The majority of SPINK7 modified genes (77%) were also differentially expressed during differentiation, including a regulator of terminal epidermal differentiation calmodulin-like 5 (CALML5), and the cornified envelope components expressed by differentiated keratinocytes such as FLG and LOR (data not shown) (Sun, B. K. et al. *Genes & development* 29, 2225-2230 (2015)). Importantly, the top genes which were overexpressed during differentiation were down-regulated after SPINK7 silencing. This indicated that loss of SPINK7 promoted transcriptional changes that resulted in an undifferentiated epithelial phenotype.

Figure 3A:
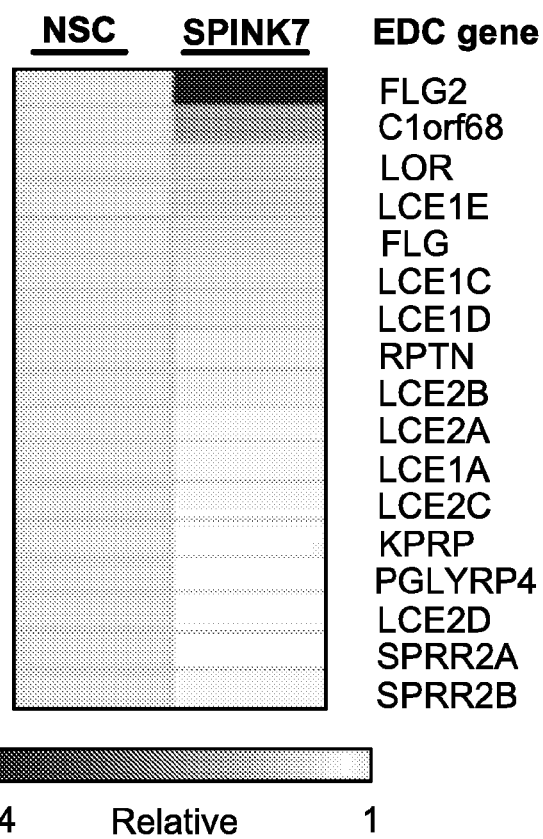
FIG. 3A shows a heatmap representing the fold change of 17 EDC genes that are significantly ($p<0.05$) altered by SPINK7 depletion in EPC2 cells following ALI differentiation (day 14).
Figure 3B:
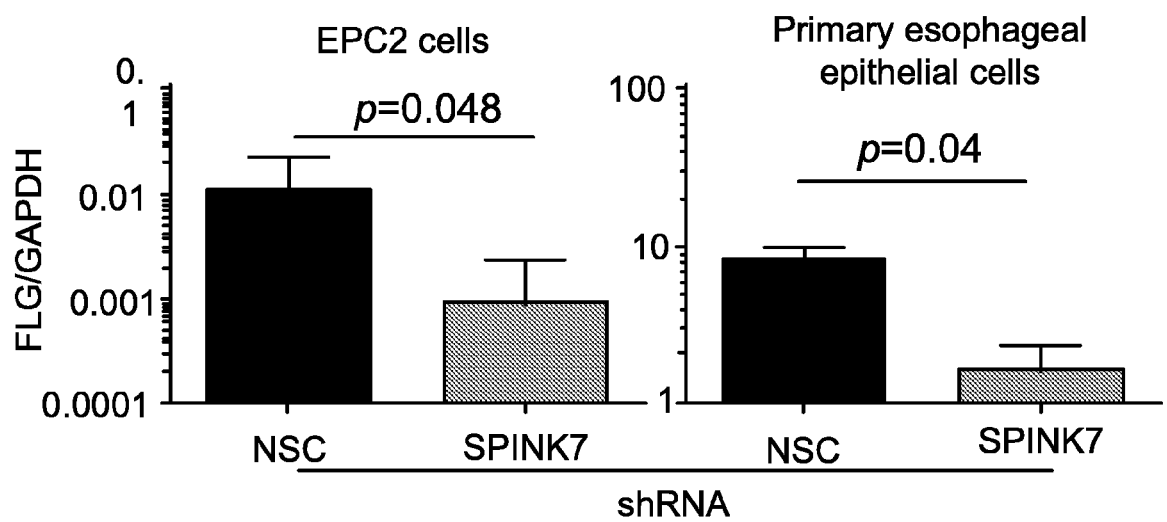
FIG. 3B is a bar graph showing FLG mRNA expression in NSC or SPINK7-depleted EPC2 or primary esophageal epithelial cells following ALI differentiation from three independent experiments performed in triplicates.
Figure 3C:
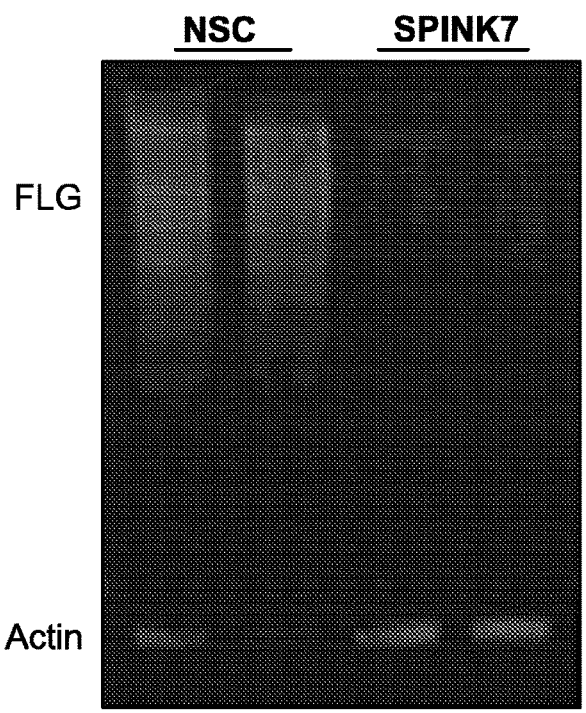
FIG. 3C is a gel showing filaggrin protein expression in NSC or SPINK7-depleted EPC2 cells following ALI differentiation was assessed by western blot.

Focusing on the epidermal differentiation complex (EDC) locus on 1q21, the locus with the greatest change in expression in the EoE transcriptome, the genes altered by SPINK7 silencing and the EDC genes were intersected (Blanchard, C. et al. *Journal of immunology* 184, 4033-4041 (2010)). Of the 54 EDC genes expressed by differentiated epithelial cells (RPKM>1), 17 genes were significantly down-regulated by SPINK7 loss (FIG. 3A). SPINK7 silencing resulted in a marked decrease in filaggrin mRNA (FIG. 3B) and protein expression as shown by western blot and immunofluorescence analyses (FIG. 3C) analyses. Notably, the expression of SPINK7 and FLG correlated in EoE patients (n=133) (data not shown).

Venn diagrams depicting the number of genes differentially expressed (<2-fold, p<0.05, FPKM>1) in SPINK7 gene silencing as compared to NSC in EPC2 cells differentiated ALI cultures for 14 days (SPINK7—269 genes) and in EPC2 cells following ALI differentiation (day 14 of culture) compared to prior ALI differentiation (day 7 of culture) (Terminal differentiation—678 genes) (data not shown) or in EPC2 cells following ALI differentiation (day 14 of culture) compared cells in monolayer (day 0) (differentiation-3225 genes) (data not shown). Genes overlapping between these two data sets were identified. The top 14 genes with the highest decrease in expression are presented. Ten epidermal differentiation complex (EDC) genes were significantly (p<0.05) altered by SPINK7 depletion in EPC2 cells following ALI differentiation (day 14). FLG mRNA expression in NSC or SPINK7-depleted EPC2 cells following ALI differentiation (data not shown; data represented as the mean±Sd from three independent experiments performed in triplicates). Correlation of normalized FLG and normalized SPINK7 expression in esophageal biopsies of 170 patients with active EoE was also performed (data not shown).

Example 4: SPINK7 Regulation is Upstream of SPINK5 in Esophageal Cells

Figure 4A:
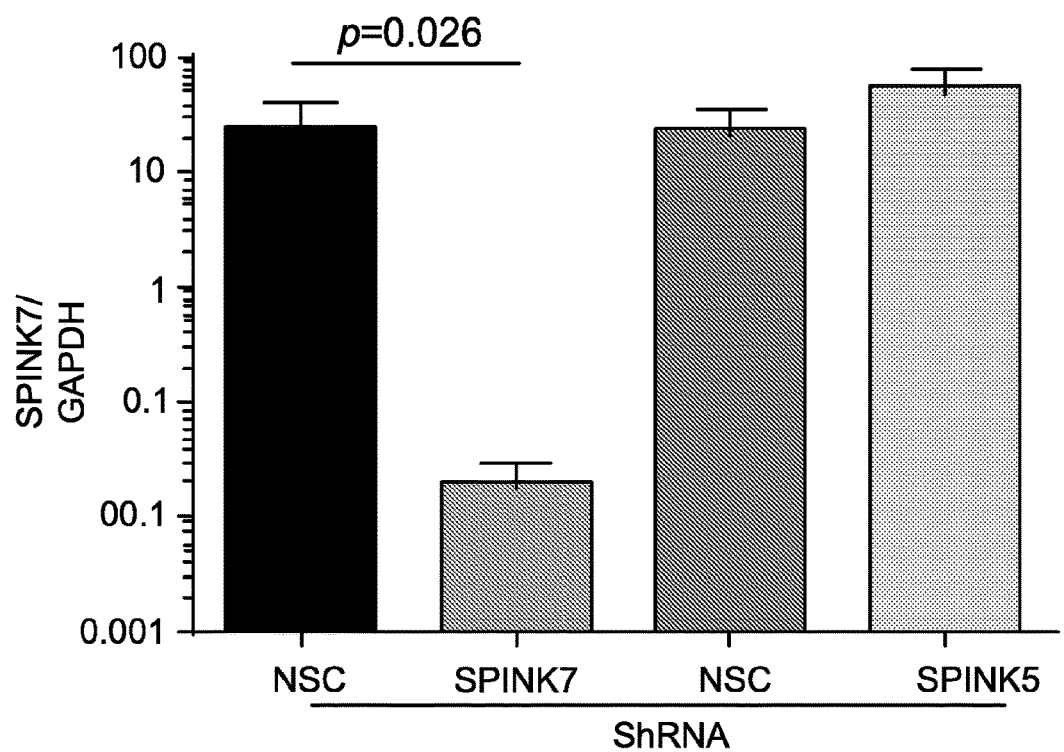
FIGS. 4A and 4B are bar graphs showing qPCR analysis of SPINK7 expression (FIG. 4A), or SPINK5 expression (FIG. 4B) of control (NSC), SPINK7-depleted and SPINK5-depleted EPC2 cells that were grown for 14 days in ALI culture.
Figure 4B:
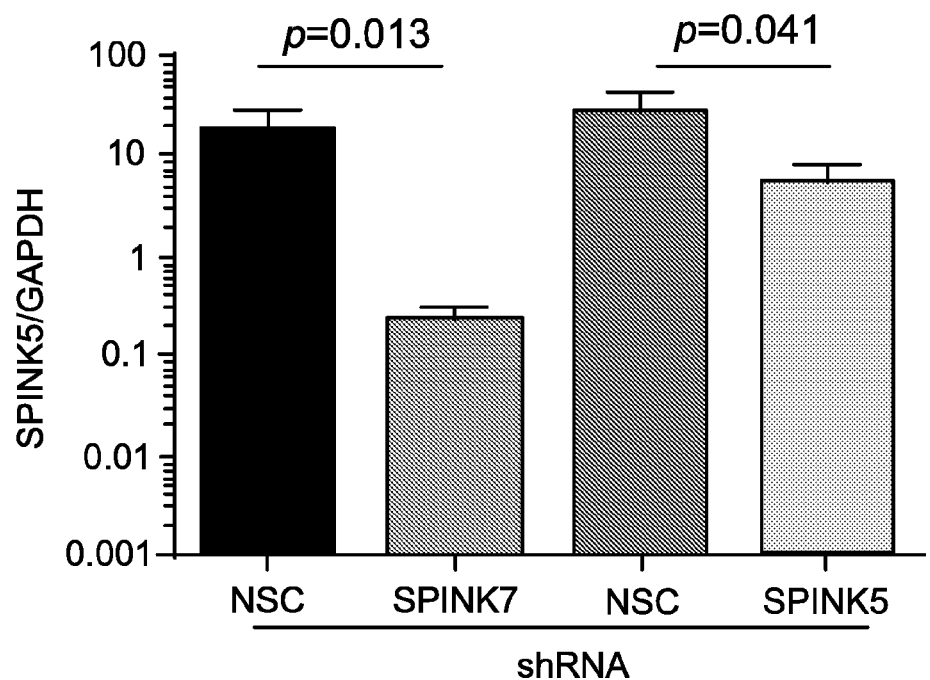

Having identified SPINK5 as part of the epithelial differentiation program (FIG. 2), the impact of SPINK7 silencing on SPINK5 expression was examined. In contrast to the absence of the effect of SPINK7 downregulation on SPINK5 mRNA level in undifferentiated EPC2 cells, SPINK7 silencing markedly reduced the expression of SPINK5 mRNA following ALI differentiation (88-fold decrease; FIG. 4B). In contrast, SPINK5 silencing did not affect SPINK7 expression (FIG. 4A). These data suggest that loss of SPINK7 expression may be upstream of loss of SPINK5.

Example 5: Silencing of SPINK7 Results in Transcriptional Changes that Overlap with the EoE and IL-13-Associated Transcriptomes The impact of loss of SPINK7 on the EoE transcriptome, the abnormal transcriptional profile of the esophagus of EoE patients was analyzed. The genes modified by SPINK7 silencing in differentiated cells were intersected with the EoE transcriptome and a substantial overlap of 36% was found (data not shown). These genes were enriched for abnormal skin inflammation, skin physiology, skin development and innate immune response (FIG. 5A) including major histocompatibility complex (MHC) genes, FLG, interferon induced with helicase C domain 1 (IFIH1) and IL36RN (data not shown).

Because it had been demonstrated that EoE pathogenesis is mediated at least in part by an IL-13-stimulated keratinocyte-derived transcriptome (Blanchard, C. et al. *The Journal of allergy and clinical immunology* 120, 1292-1300 (2007), and Kc, K., Rothenberg, et al *PloS one* 10, e0127755

(2015)), the genes modified by SPINK7 silencing were intersected with the genes modified by IL-13-treatment in EPC2 cells following ALI differentiation based on genome-wide RNA sequencing data (Kc, K., Rothenberg, et al *PloS one* 10, e0127755 (2015)). One hundred nineteen genes overlapped between these two transcript profiles (data not shown). These genes were enriched for abnormal skin including keratosis and acantholysis, skin development and differentiation as well as innate immunity (data not shown).

Analysis of the localization of these proteins revealed significant enrichment in the cornified envelope (data not shown). Further, 48% of the overlapping genes between SPINK7-regulated transcripts and EoE transcriptome were regulated by IL-13 (FIG. 5B), indicating that SPINK7 interplays between the two pathways although IL-13 did not down-regulated SPINK7 (data not shown).

A Venn diagram was made depicting the number of genes differentially expressed in EoE patients as compared to control (<2-fold, p<0.05, FPKM>1) (EoE—1607 genes) and in SPINK7 gene silencing as compared to NSC in EPC2 cells differentiated ALI cultures for 14 days (SPINK7—269 genes) identified by RNA sequencing (data not shown). Genes overlapping between these two data sets were identified (86 genes). A heatmap of the overlap gene is presented according to their fold changed expression after SPINK7 silencing as compared to control (SPINK7) and fold changed expression in EoE as compared to control. A Venn diagram was made depicting the number of genes differentially expressed by EPC2 cells following ALI differentiation after IL-13 stimulation compared to untreated cells (<2-fold, p<0.05, FPKM>1) (EoE—1161 genes) and in SPINK7 gene silencing as compared to NSC in EPC2 cells differentiated ALI cultures for 14 days (SPINK7—269 genes) identified by RNA sequencing. Genes overlapping between these two data sets were identified (80 genes) (data not shown). A Venn diagram was made depicting the number of genes that overlap between EoE and SPINK7 silencing (EoE/SPINK7—86 genes) and the number of genes that overlap between IL-13 trigger and SPINK7 silencing (IL-13/SPINK7—80 genes) (data not shown). Genes overlapping between these two data sets were identified (41 genes).

Example 6: Loss of SPINK7 Induces Epithelial Architecture

Figure 6A:
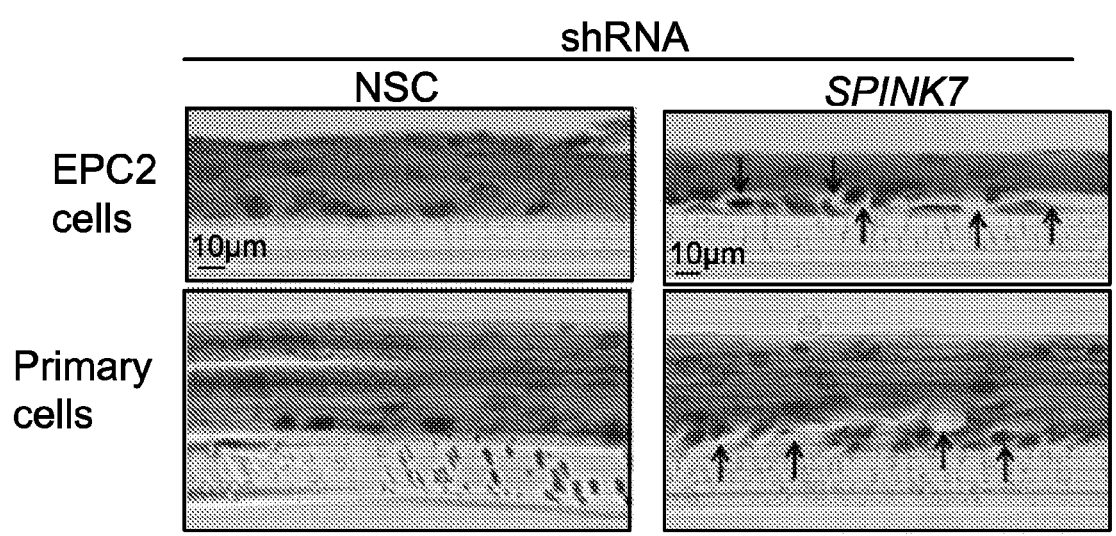
FIGS. 6A-6C show that loss of SPINK7 impairs epithelial architecture and epithelial barrier function.

SPINK7 silencing resulted in dilated intercellular spaces compared with NSC treated cells after ALI differentiation (day 14) (see arrows in FIG. 6A). Analysis of the non-associated areas revealed that SPINK7-depleted ALI cultures had a 3-fold increase (p=0.0002) in the non-cell associated tissue area compared with NSC ALI cultures (data not shown). Quantitative analyses was performed of H&E sections from NSC or SPINK7-depleted EPC2 cells following ALI differentiation and were presented as the mean volume of tissue area per a high power field minus the non-cell associate areas that were formed inside the tissues, per a high power field (data not shown), the percent of non-cell associate areas in the tissues measured as the ratio between the non-cell associate areas per high power filed and the total tissue area per a high power field.

As a control, morphometric analysis of the total area of the differentiated ALI cultures was not altered after SPINK7 silencing compared to NSC (data not shown), the percent of non-cell associate areas in the tissues measured as the ratio between the non-cell associate areas per high power filed and the total tissue area per a high power field. Data are representative of three experiments performed in triplicate and are represented as the mean±Sd. Quantitative analysis of H&E-stained sections was performed of NSC or SPINK7-depleted EPC2 cells grown for 7, 9 and 11 days in the ALI cultures (data not shown). The percent of non-cell associate areas in the tissues was quantified from three experiments performed in triplicate and are represented as the mean±Sd.

Figure 6B:
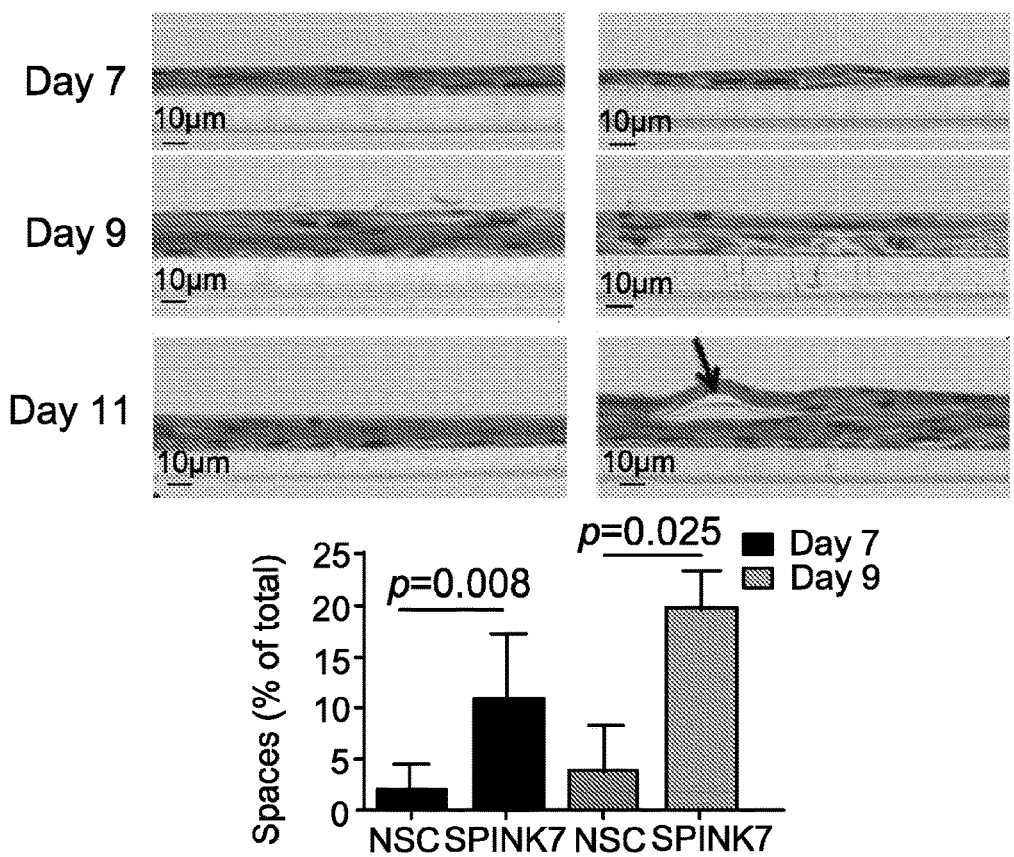
Figure 6C:
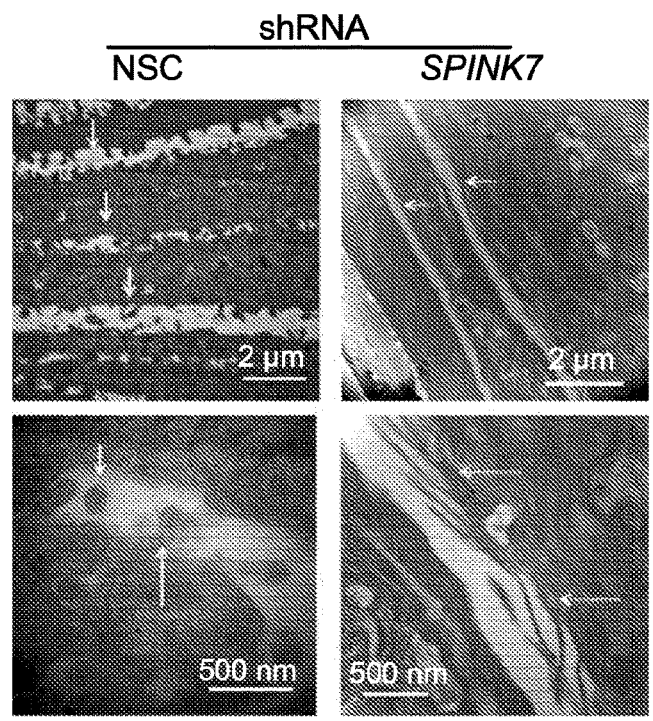

At baseline (day 7), SPINK7 silencing increased non-cellular spaces by 5.4-fold (p=0.008) compared to NSC control cells that were densely packed (FIG. 6B). The same finding was observed in SPINK7-silenced cells at day 9 (5.4-fold, p=0.025) (FIG. 6B). Notably, by 11-14 days, blebbing of the squamous layers was seen following SPINK7 silencing (see arrow in FIG. 6B). Transmission electron microscopy revealed that the microplicae, intercellular ridges and finger like projections between cells that were readily apparent in the NSC cells were nearly absent from SPINK7-silenced cells (FIG. 6C)

Example 7: SPINK7 Silencing Results in Alterations of Junctional Proteins

Figure 7:
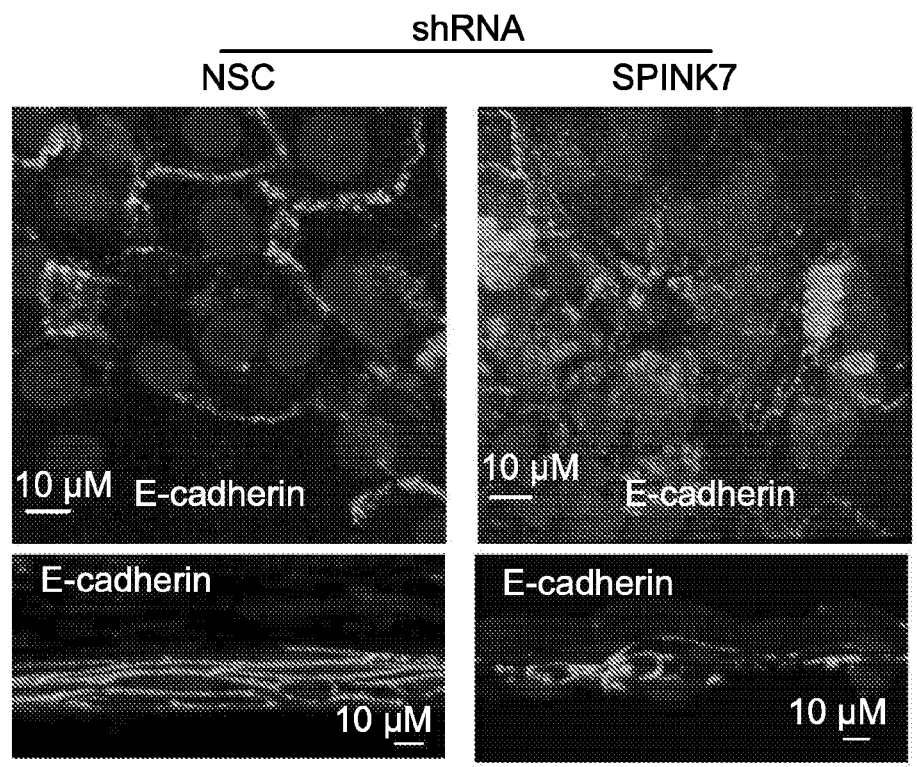
FIG. 7 shows immunostained sections of E-cadherin and DAPI of NSC or SPINK7-depleted EPC2 cells grown with high $Ca_{2+}$ or following 14 days of ALI differentiations (bottom).

Immunofluorescence analysis of submerged as well as ALI cultures of EPC2 cells revealed that E-cadherin localized to the cellular membrane and showed an organized pattern of cellular junctions (FIG. 7). The localization of β-catenin, the E-cadherin effector, was adjacent to the cells membranes (data not shown). Following SPINK7 silencing, E-cadherin was diffusely present within cells and the cellular membrane, and the staining was often found in aggregates. β-catenin was partially localized to the cytoplasm and partially remained localized in cell periphery (FIG. 7).

Immunofluorescence analysis of DSG1 expression in ALI cultures of control cells revealed membrane localization. In contrast, after SPINK7 silencing, DSG1 expression was decreased and abnormally localized in the cytoplasm (data not shown).

Example 8: SPINK7 Silencing Induced IBF

Figure 8:
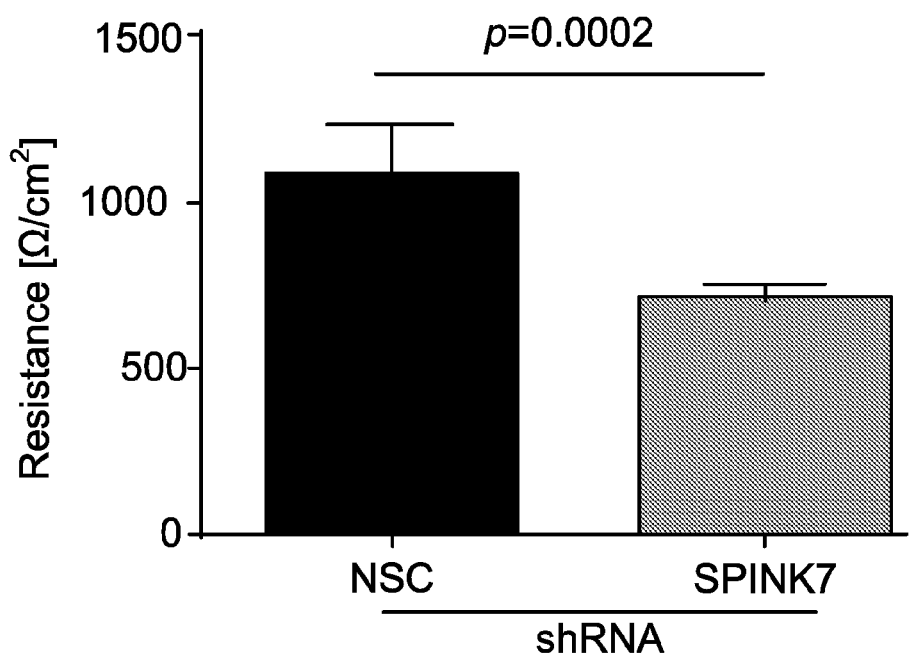
FIG. 8 shows transepithelial electrical resistance ($\Omega$) was measure from NSC and SPINK7-depleted EPC2 cells at day 7 of ALI differentiation.

Paracellular and transcellular permeability of the ALI cultured cells were analyzed. Transepithelial electrical resistance (TEER) was reduced by 36% during ALI differentiation of SPINK7-depleted cells compared to NSC cells (FIG. 8). Transepithelial electrical resistance (Ω) was measured from NSC and SPINK7-depleted EPC2 cells measured at day 7 and 8 during ALI differentiation (data not shown; data were representative of four experiments performed in triplicate and are represented as the mean±Sd). These data reveal that down regulation of SPINK7 expression was sufficient to induce IBF.

Example 9: SPINK7 Gene Silencing Unleashes the Production of Pro-Inflammatory Cytokines The supernatant of SPINK7 silenced cells was analyzed using a multiplex cytokine array. Amongst 64 cytokines, a marked change in 18 cytokines (FIG. 9A) was observed. Amongst the changes, IL-8 was increased by 12-fold (p=0.03) in the SPINK7-depleted cells compared to NSC cells (FIG. 9A); and this was verified by ELISA and qPCR analyses (data not shown). Interestingly, there was a negative correlation between SPINK7 and IL-8 mRNA expression in a cohort of 133 EoE patients (p=0.014; data not shown), supporting the inverse relationship between SPINK7 and IL-8.

In addition, IL-8 expression increased in EoE patients compared to controls (data not shown) (Persad, R. et al.

*Journal of pediatric gastroenterology and nutrition* 55, 251-260 (2012), and Blanchard, C. et al. *The Journal of allergy and clinical immunology* 127, 208-217, 217 e201-207 (2011)). IL-8 release was blocked by cyclosporine A (CsA) and FK506 (FIG. 9B), suggesting that the increase cytokine release is mediated through NFAT activation. Indeed, NFATC1 was translocated to the nucleus after SPINK7 silencing compared to NSC cells (data not shown).

Multiplex cytokine array analysis of the supernatant of SPINK7 silenced cells and controls that were treated with CsA revealed that CsA partially blocked the release of several cytokines including eotaxin-1 and IL-16 while other cytokines such as G-CSF and IL-15 remained unaffected (data not shown). Notably, CsA did not affect the proteolytic activity or the barrier function (data not shown). Consistent with these findings, human eosinophils showed increased chemotaxis towards supernatants derived from SPINK7-silenced cells as compared to supernatants derived from NSC cells or media alone (data not shown).

Figure 9A:
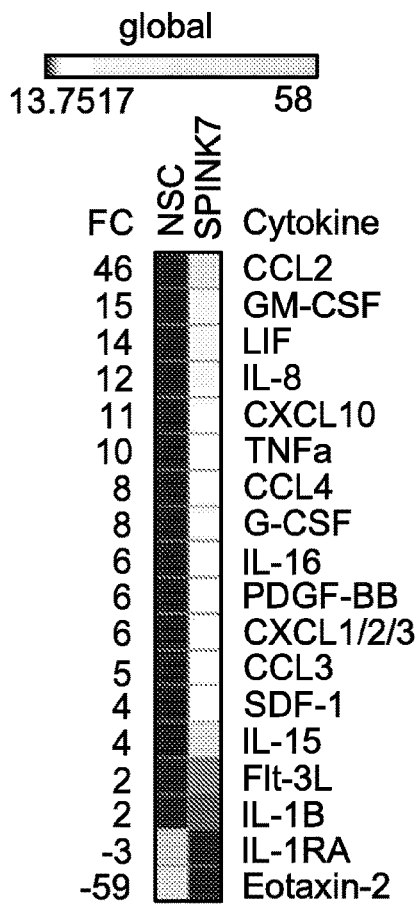
FIGS. 9A-9C show that the loss of SPINK7 induces cytokine expression and release.
Figure 9B:
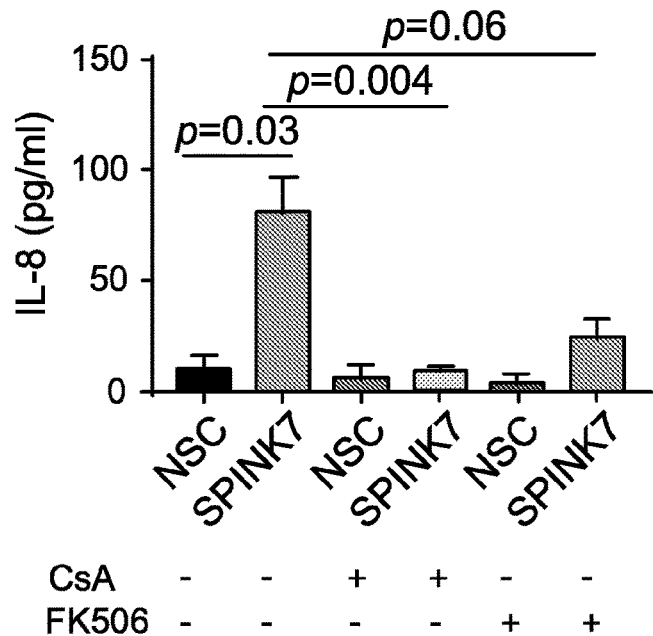
Figure 9C:
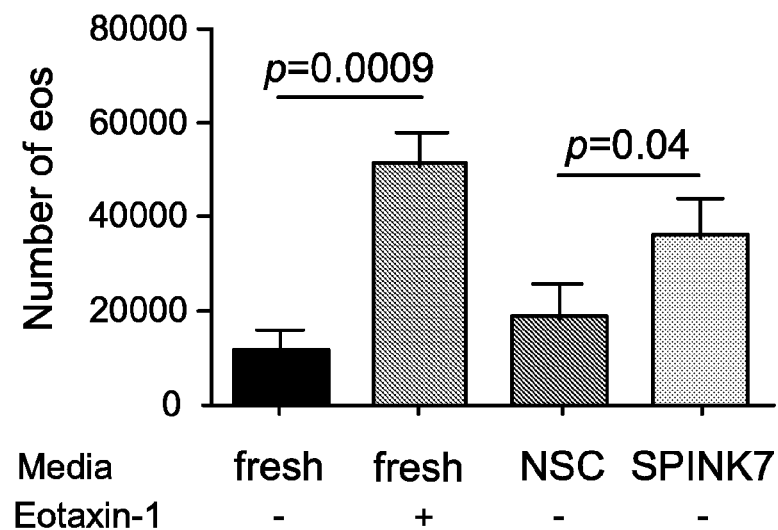

FIG. 9A shows a heatmap of cytokine and chemokine expression derived from supernatants of NSC or SPINK7-depleted EPC2 cells following ALI differentiation (day 14) that were altered Con>1 pg/mL, −2>Fold Change (FC)>2, P<0.05) after SPINK7-depletion as compared to NSC. Data presented as the mean of two independent experiments performed in quadrats. IL-8 protein expression in supernatants (data not shown) and mRNA expression from NSC or SPINK7-depleted EPC2 cells following ALI differentiation (day 14) was performed. Data represented as the mean±Sd from three independent experiments performed in triplicates. TSLP protein expression in supernatants from NSC or SPINK7-depleted EPC2 cells following ALI differentiation was performed (data not shown).

Example 10: Impact of SPINK7 Silencing on Serine Proteinases

Figure 10A:
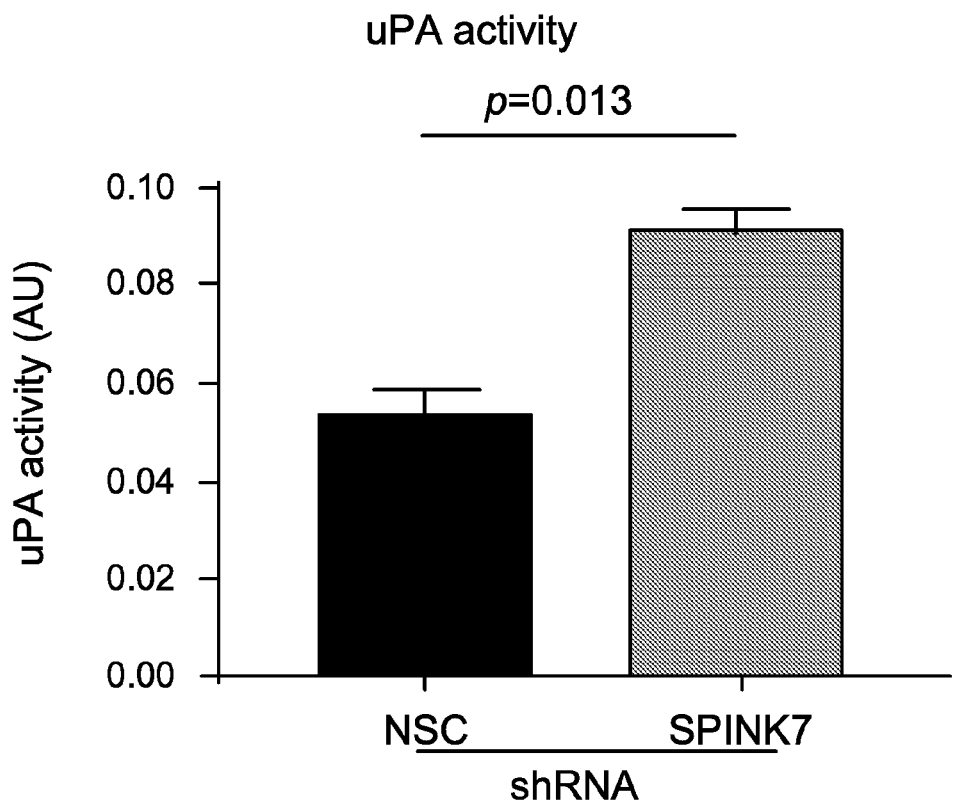
FIGS. 10A-10E show that A1AT administration reverses the aggravated inflamed mucosa and impaired barrier in SPINK7-deleted cells and shows evidence that uPA/uPAR is involved in human EoE.

The known SPINK7 target uPA (Cheng, X., Lu, S. H. & Cui, Y. *Cancer letters* 290, 87-95 (2010), and Huang, G. et al. *Carcinogenesis* 28, 2274-2281 (2007)) was analyzed. Consistent with previous reports, SPINK7 directly inhibited uPA proteolytic activity (data not shown) (Cui, Y., et al *International journal of oncology* 37, 1521-1528 (2010)). In addition, supernatants from cells during differentiation revealed a 1.8-fold increase in released uPA activity after SPINK7 silencing (p=0.013) (FIG. 10A). An increased proteolytic activity using the broad trypsin-like activity substrate Val-Pro-Arg (FIG. 10B) was observed.

Figure 10B:
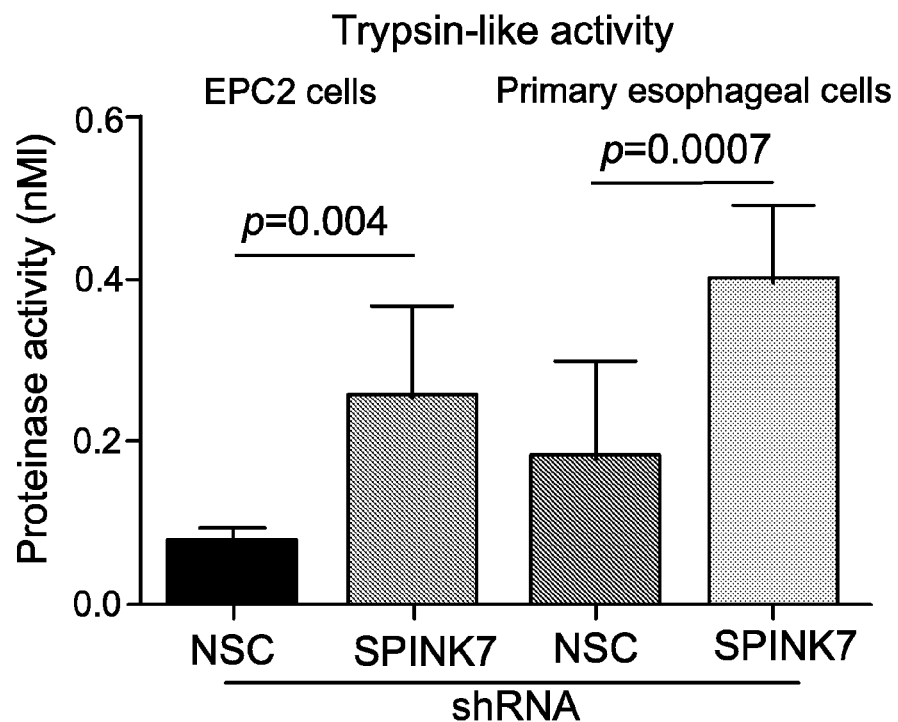
Figure 10C:
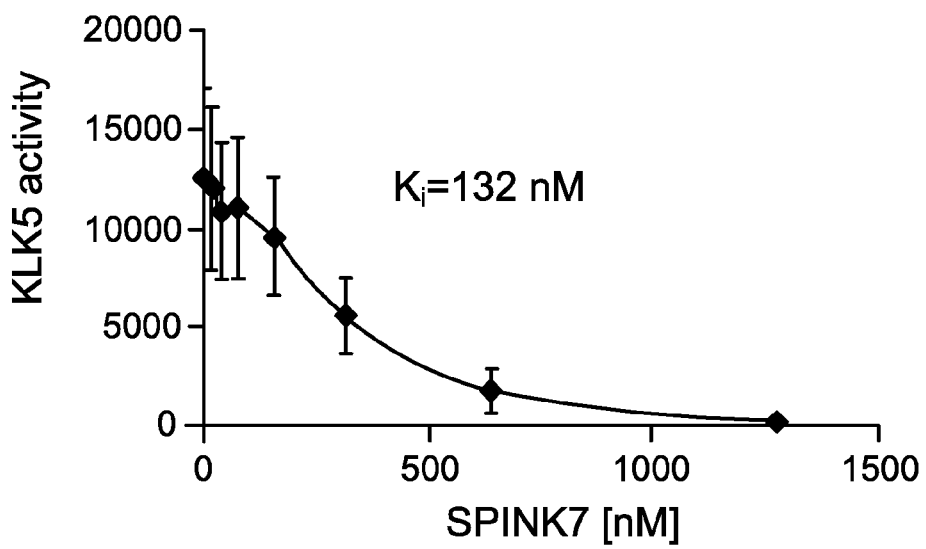
Figure 10D:
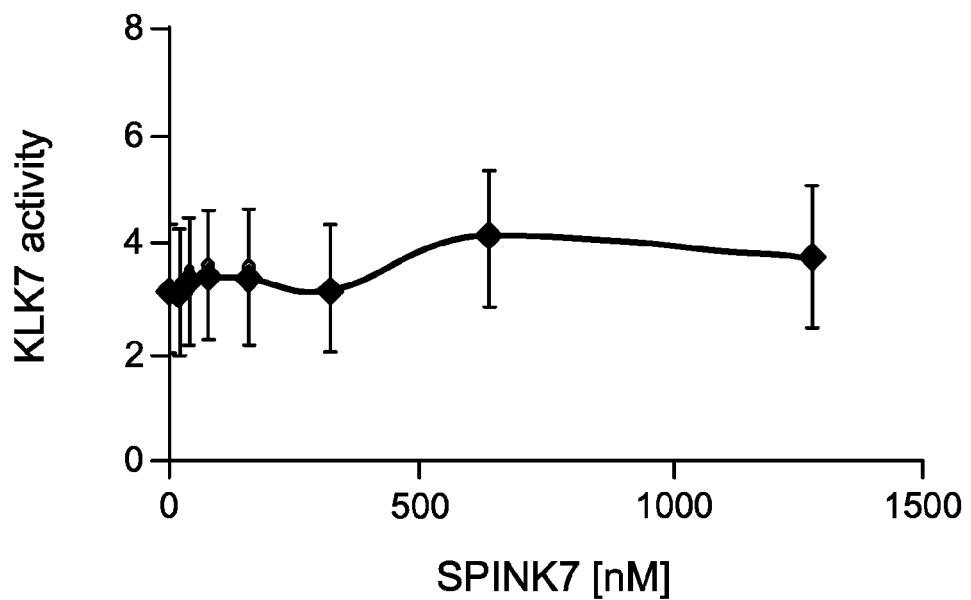
Figure 10E:
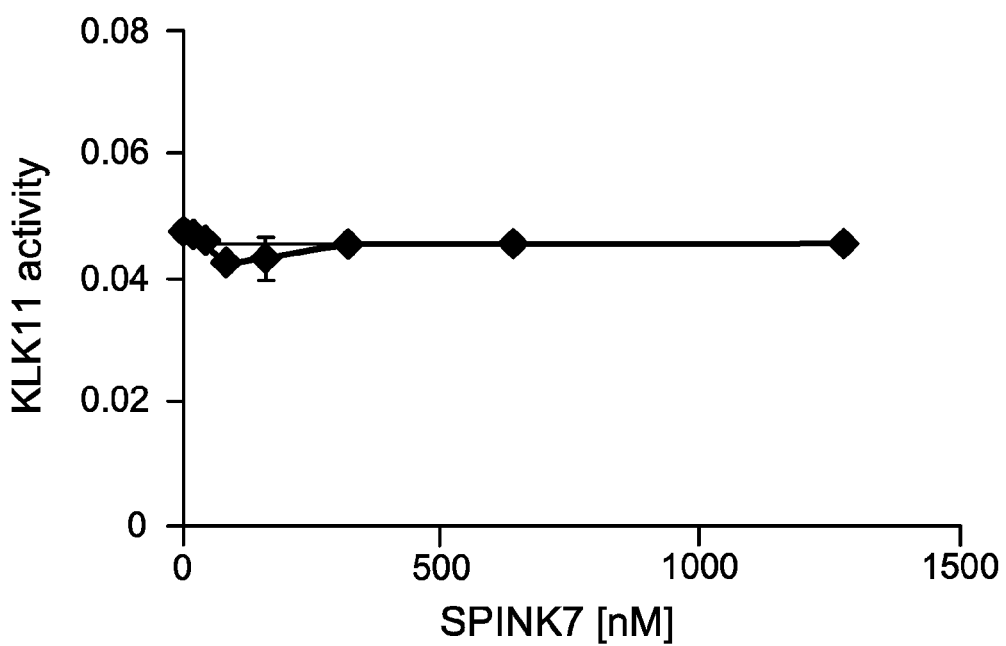

Given that most members of the KLK family have trypsin-like activity, the ability of SPINK7 to directly inhibit members from this family in vitro was tested. SPINK7 inhibited KLK5 proteolytic activity in a dose-dependent manner with a mean $K_i$ of 132±108 nM (mean±SD) (FIG. 10C) but did not inhibit KLK7 and KLK11 (FIG. 10D and). SPINK7 silencing did not increase proteinase protein expression (data not shown) indicating that the unleashed proteinase activity was simply related to loss of proteolytic inhibition. Collectively, these data indicated that SPINK7 directly inhibits serine proteinases including uPA and KLK5, while SPINK7 gene silencing results in increase proteolytic activity of uPA and KLKs.

qPCR analysis was performed of SPINK7 and SPINK5 expression of control (NSC) or SPINK7-depleted EPC2 cells that were grown in a monolayer or differentiated in ALI culture (data not shown). Panel B shows quantification of uPA activity in supernatants derived from (NSC) or SPINK7-depleted EPC2 cells following ALI differentiation. Data are representative of three experiments performed in triplicate and are represented as the mean±Sd. FIG. 12G shows quantification of the activity of serine proteinases with trypsin-like activity in supernatants derived from (NSC) or SPINK7-depleted EPC2 cells following ALI differentiation. Data are representative of four experiments performed in triplicate and are represented as the mean±Sd. FIGS. 10A and 10B show in vitro activity assays of KLK5, KLK7 and KLK11 in the presence of the indicated concentrations of SPINK7. Data are representative of three experiments and are represented as the mean±s.e.m.

Example 11: Gene Silencing of SPINK7 Results in Alteration in Adherens Proteins and Desmosomal Proteins Followed by Impaired Epithelial Barrier Confocal microscopic analysis of high resolution 3D structures of differentiated cells revealed that DSG1 and E-cadherin staining was limited to membranes in the superficial regions of the NSC cells and demonstrated close association between the cells. In contrast, there was marked separation after SPINK7 silencing (data not shown).

Figure 11A:
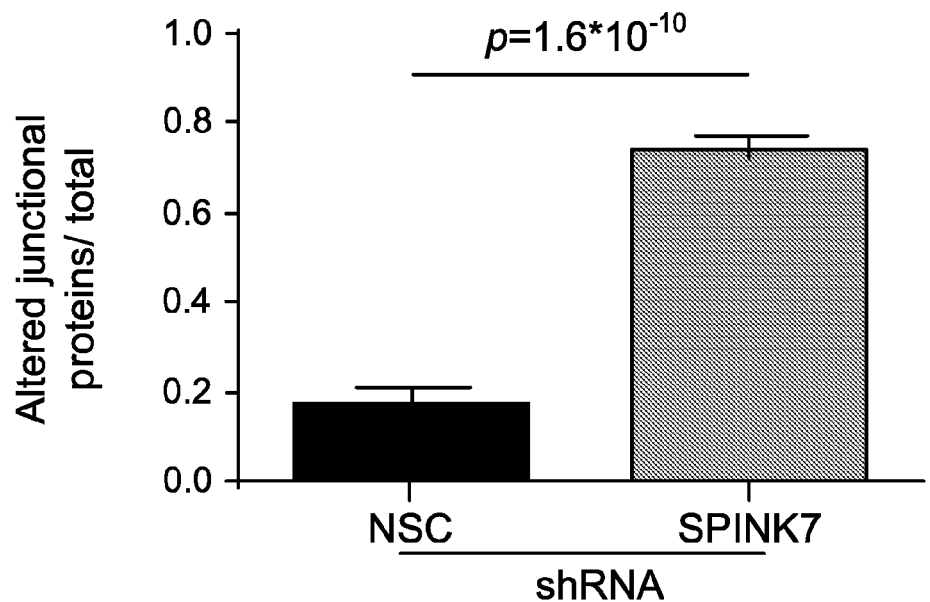
FIGS. 11A and 11B show that loss of SPINK7 impairs epithelial architecture and epithelial barrier function.
Figure 11B:
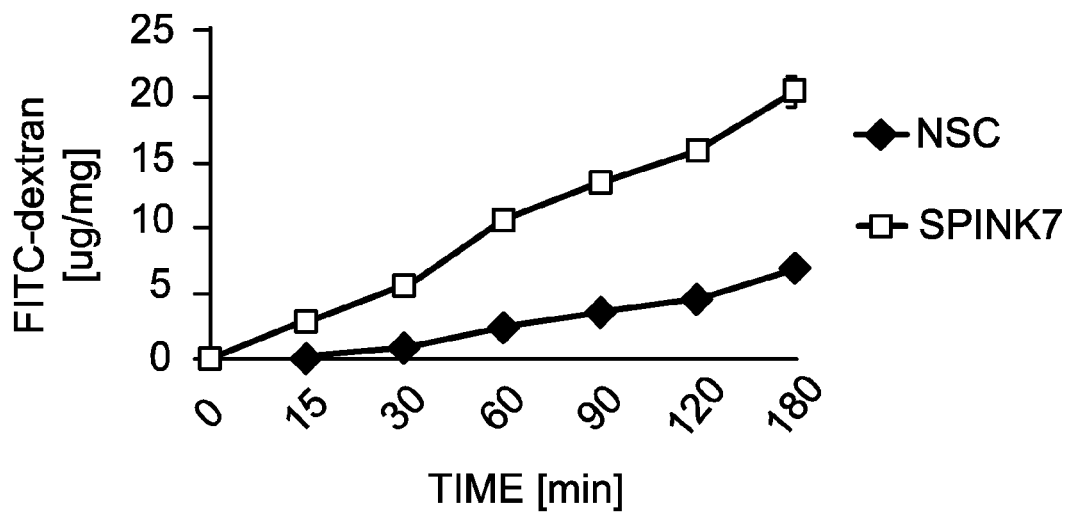

FIG. 11A shows quantitative analysis of cells demonstrating alterations of junctional proteins from the total cells from NSC or SPINK7-depleted EPC2 cells following ALI differentiation. Data are representative of four experiments performed in triplicate and are represented as the mean±Sd. FIG. 11B shows FITC-dextran flux measured at day 14 of ALI differentiation from NSC and SPINK7-depleted EPC2 cells for the indicated time points. Analysis of the transcellular permeability by measuring the flux of macromolecules (FITC-dextran) was significantly increased in SPINK7 shRNA-transduced cells compared to NSC cells and reached 2.9-fold increase (FIG. 11B).

Example 12: uPA in the Esophagus of EoE Patients

Figure 12A:
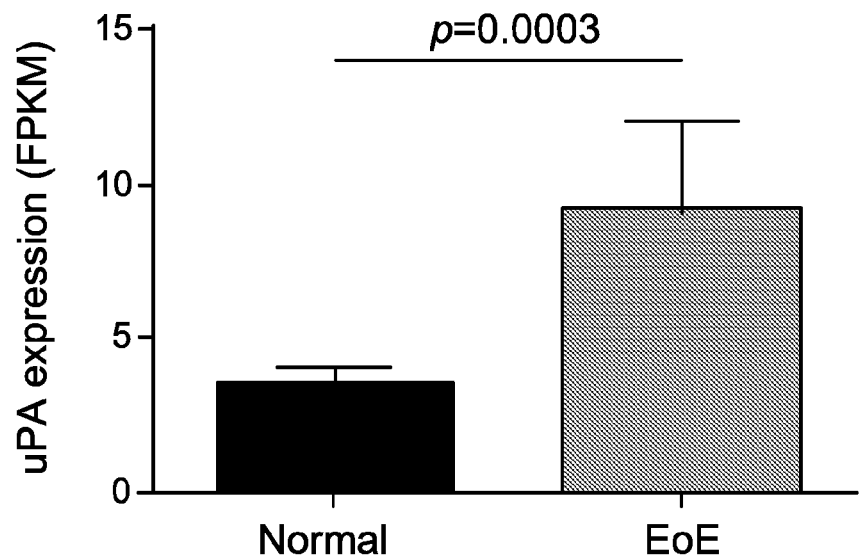
FIGS. 12A-12G show that A1AT administration reverses the aggravated inflamed mucosa and impaired barrier in SPINK7-deleted cells and shows evidence that uPA/uPAR is involved in human EoE.
Figure 12B:
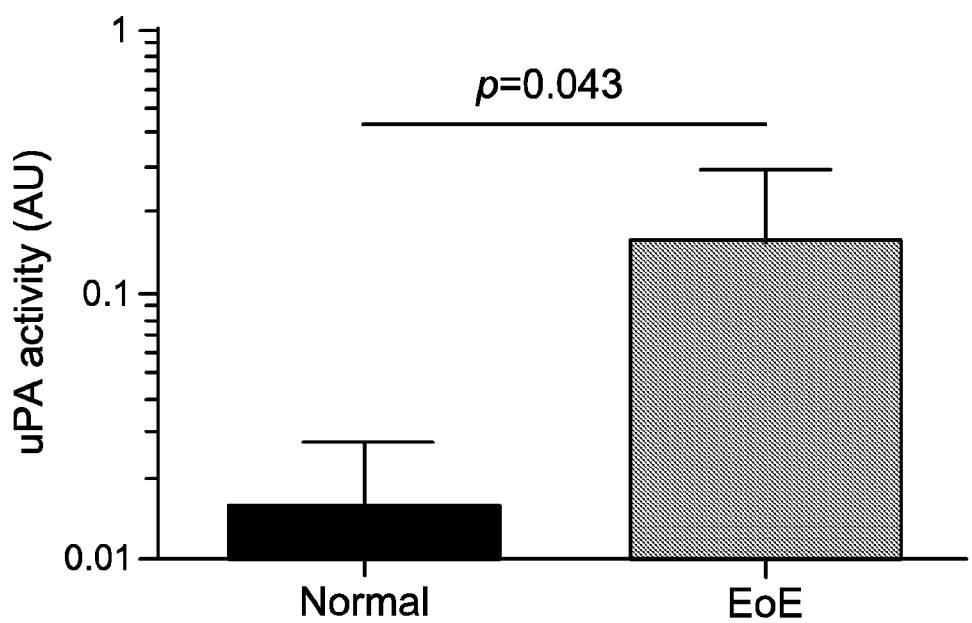
Figure 12C:
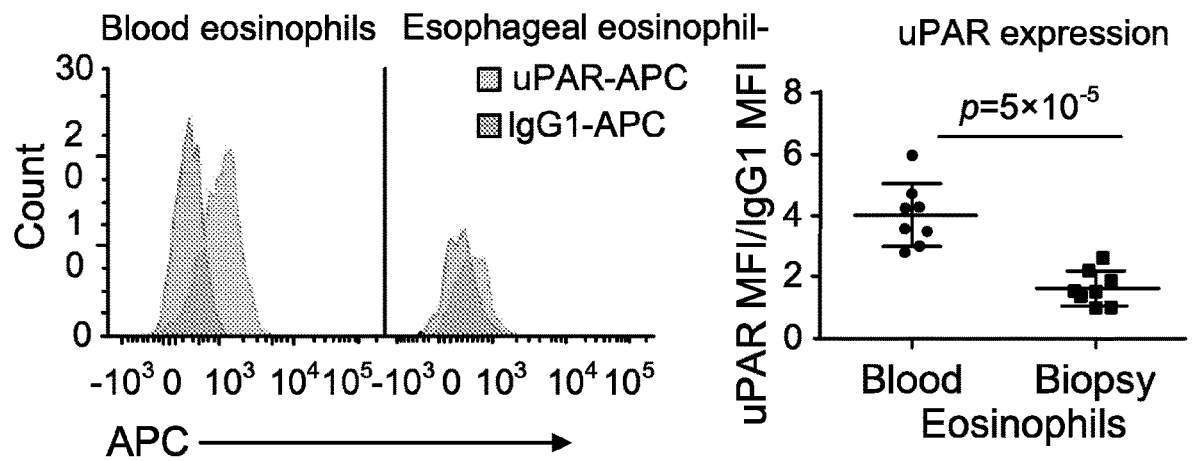

In esophageal biopsies from EoE patients, uPA mRNA expression was increased (2.7-fold; p=0.0003) and uPA activity increased by 10-fold (p=0.043) compared with control individuals (FIGS. 12A and 12B). Notably, the pan proteinase activity was not altered in EoE biopsies compared to controls (data not shown), indicating that the increased proteolytic activity observed in EoE patients was accounted by a subset of proteinases. Interestingly, uPAR expression was induced after SPINK7 silencing (data not shown). Collectively, the results provide evidence that SPINK7 mediates its function by regulating the uPA axis.

It is notable that allergic inflammatory cells including eosinophils express both uPAR and its known ligands β1 integrins (Brooks, A. M. et al. *American journal of respiratory cell and molecular biology* 35, 503-51 (2006)). In support of the involvement of this pathway in eosinophils migration, uPAR expression by esophageal eosinophils was found to be markedly decreased in the biopsies of EoE patients compared with blood eosinophils, as defined by FACS (p=5×10$^{-5}$) (FIG. 12C) (Johansson, M. W. & Mosher, D. F. *American journal of respiratory cell and molecular biology* 45, 889-897 (2011)).

Figure 12D:
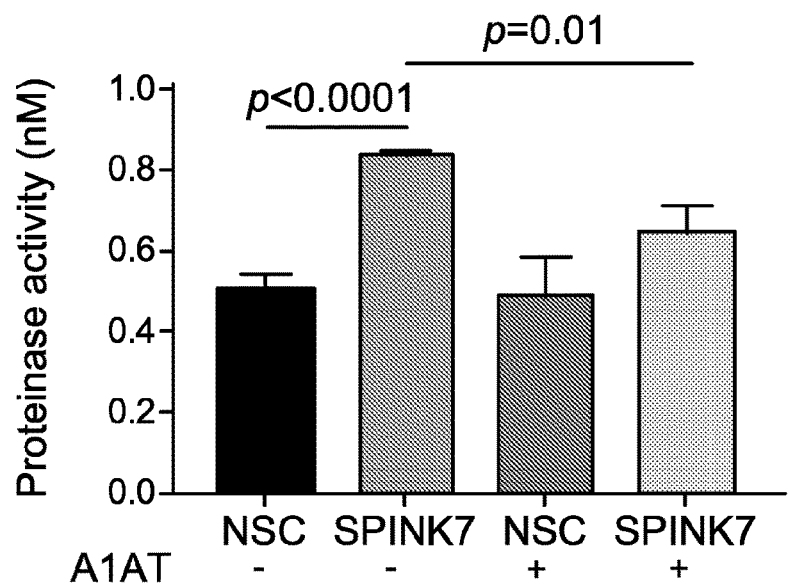

It was hypothesized that inhibition of uncontrolled proteolytic activity would ameliorate the impaired barrier and the loss of epithelial differentiation elicited by the loss of SPINK7. The serine proteinase inhibitor, α1 anti-trypsin (A1AT) is a known inhibitor of KLK5 (Goettig, P., et al. *Biochimie* 92, 1546-1567 (2010)) and has potential clinical benefit with a good safety profile in humans (Lewis, E. C. *Molecular medicine* 18, 957-970 (2012)). Administration of A1AT to the cells inhibited the trypsin-like activity of supernatant of SPINK7 silenced cells (FIG. 12D).

Figure 12E:
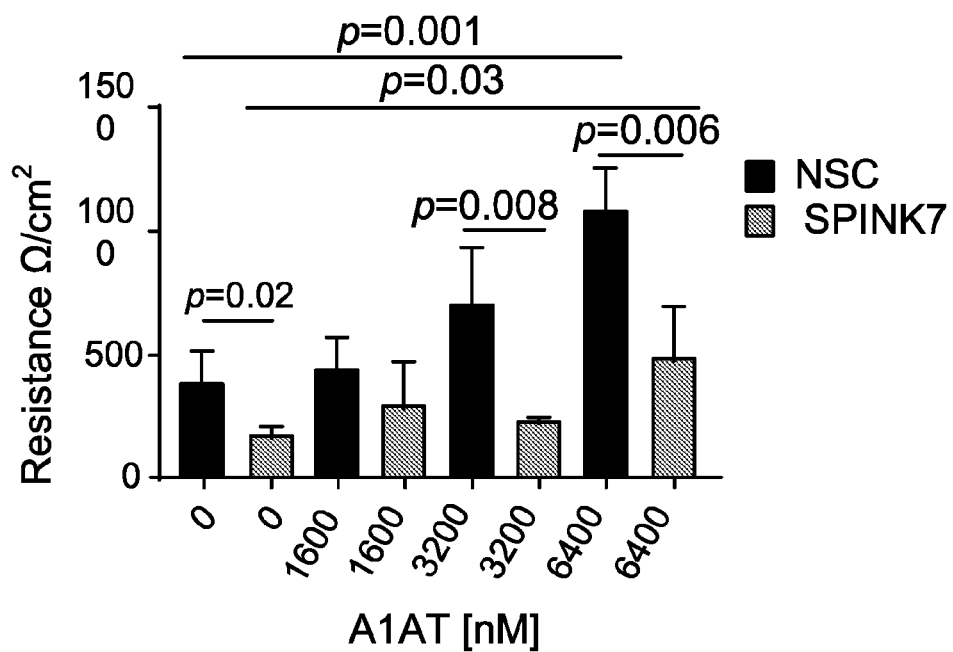
Figure 12F:
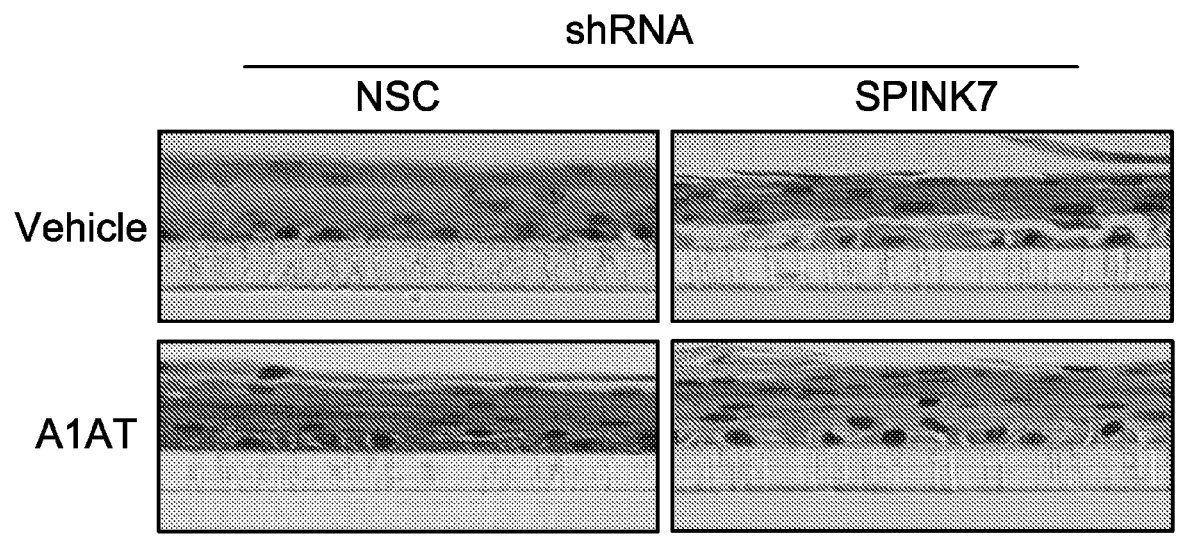
Figure 12G:
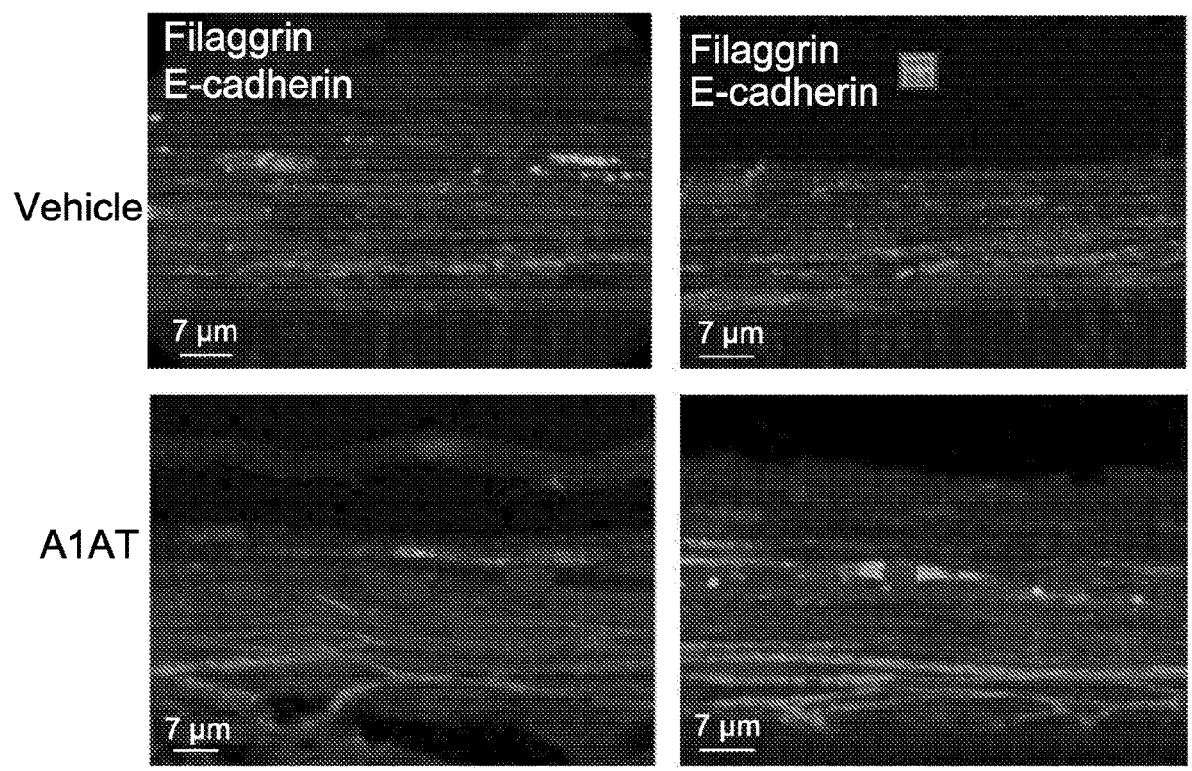
Figure 13:
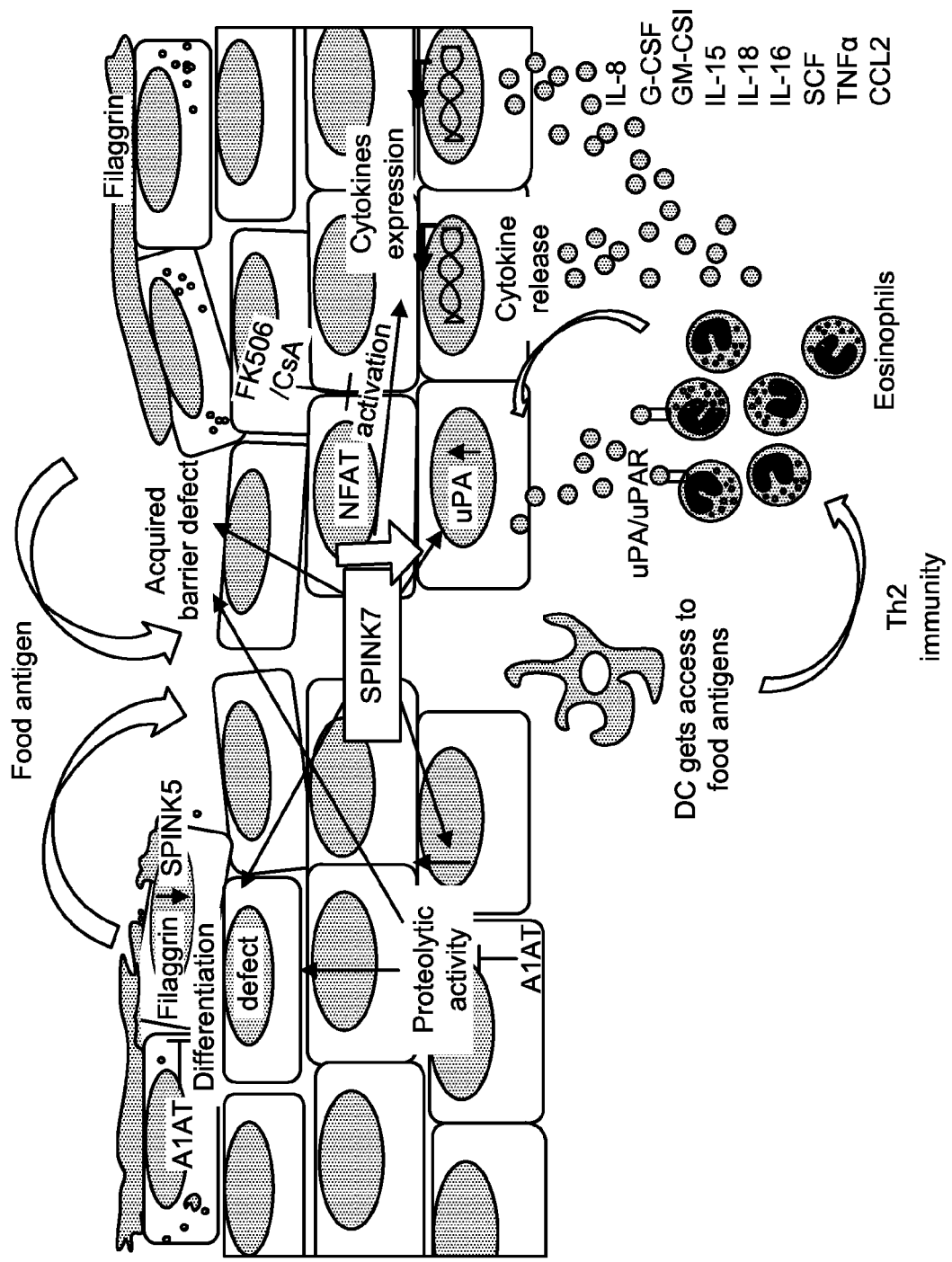
FIG. 13 shows a provisional model (a schematic model of SPINK7 anti-inflammatory checkpoint). Loss of SPINK7 resulted in uncontrolled proteolytic activity including increased uPA and KLK5 activity which promoted impaired epithelial differentiation including downregulation of SPINK5 and FLG and IBF which enabled dendritic cells (DC) to encounter luminal antigens and promote Th2 response. Restoring the controlled proteolytic activity by A1AT administration ameliorated the epithelial differentiation and barrier function. Loss of SPINK7 also promoted retention of NFATC1 in the nucleus and expression of pro-inflammatory cytokines from IL-8, G-CSF, GM-CSF, IL-15, IL-18, IL-16, SCF, TNFα and CCL2 which was partially NFATC1 dependent and can be blocked by the NFATC1 inhibitors CsA and FK506. In addition, a local increase in uPA activity facilitated eosinophil infiltration to the esophagus upon binding of uPA to uPAR.

To extend the potential benefit of A1AT, its ability to restore the epithelial changes induced by SPINK7 loss was ability. Of note, A1AT demonstrated a dose-dependent ability to improve barrier function (FIG. 12E) and epithelial integrity as demonstrated by the decreased inter-cellular spaces (FIG. 12F). Consistent with these findings, A1AT administration increased filaggrin expression (FIG. 12G)

An analysis of single nucleotide polymorphism (SNP) of 700 EoE patients as compared to 412 non-atopic non-EoE controls was performed. The results revealed significant genetic interaction between TSLP and PLAU (encoding for uPA) in EoE patients (data not shown). Further analysis showed a genetic interaction between the TSLP, PLAU and SPINK locus. FIG. 12C shows the expression of uPAR on the cell surface eosinophils derived from blood or esophageal biopsies from 8 EoE patients. FIG. 12A shows uPA FPKM values in esophageal samples from normal and EoE patients. FIG. 12B shows analysis of the uPA proteolytic activity in esophageal biopsies from normal and EoE patients.

Example 13: Genetic Epistasis Between SPINK7 and ILRL1 (ST2)

To independently prove association between SPINK7 and the pathophysiology of allergic inflammation the contribution of genetic variation of SPINK7 to EoE susceptibility was determined. The genomic coordinates of SNPs in SPINK7 genomic region were intersected with a large collection of functional genomics datasets according to ENCODE data. Based on that analysis three SNPs (i.e. rs2400509, rs3749690, r512521065) were chosen in the SPINK7 gene region that were likely to influence gene regulatory mechanisms. These SNPs were genotyped in the SPINK7 gene region in an EoE (n=501) and non-EoE allergic control cohort (n=610; data not shown). Logistic regression analysis did not reveal association with EoE susceptibility (data not shown), consistent with the recent GWAS which did not reveal association at the SPINK loci (Kottyan, L. C. et al. *Nature genetics* 46, 895-900 (2014)).

SPINK7 contributed to EoE susceptibility by interacting with other genes. As such, genetic epistasis between these SNPs and atopy-associated genes (n=79) using a custom high density SNP chip platform was identified. Analysis of EoE cases versus non-EoE allergic controls revealed significant genetic interaction between SPINK7 and genetic variants encoding for TH2-associated molecules including ST2, IL-17A, TGFβ1, TGFBR1 and epithelial genes SPRRA1 and PDE4B (data not shown). Stratified logistic regression analyses revealed that SPINK7 (rs2400509) and ST2 (rs4988958) strongly interacted (p=0.0004). Having the SPINK7 major allele in association with the minor allele of ST2 increased the risk for EoE compared to SPINK7 and ST2 minor alleles (OR 1.96; p-value<0.01) (data not shown). Analysis of EoE probability indicated that the direction of the effect for ST2 differs based on the presence of the SPINK7 allele (data not shown).

Example 14: Genetic Data Links the SPINK7 Downstream Target-uPA to EoE

TSLP, located at 5q22, is an established EoE-associated genetic locus (Sherrill, J. D. et al. *The Journal of allergy and clinical immunology* 126, 160-165 e163, (2010)). Logistic regression analysis between TSLP and atopy-associated genes on the SNP chip was performed. The most substantial SNPs that interacted with TSLP were three PLAU variants (rs2459449, rs2227551, rs2227564; p<0.0001 for each; data not shown). To understand this interaction, TSLP stratified logistic regression analyses was performed for these three PLAU variants and it was found that having the TSLP risk variant in association with the minor allele in PLAU was protective (OR 0.68-0.71; p-value range 0.011-0.004) while in those who did not have the risk variant, the minor allele in PLAU was associated with an increased risk of EoE (OR 1.99-2.10; p value range 0.0004-0.0003) (data not shown).

Example 15: Effect of Organic Compounds on KLK5 Activity

Figure 14A:
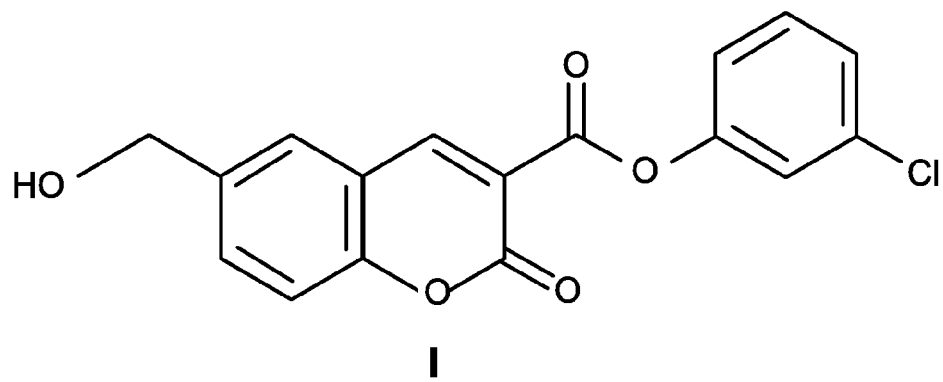
FIGS. 14A-14D show the effect of organic compounds on KLK5 activity.
Figure 14B:
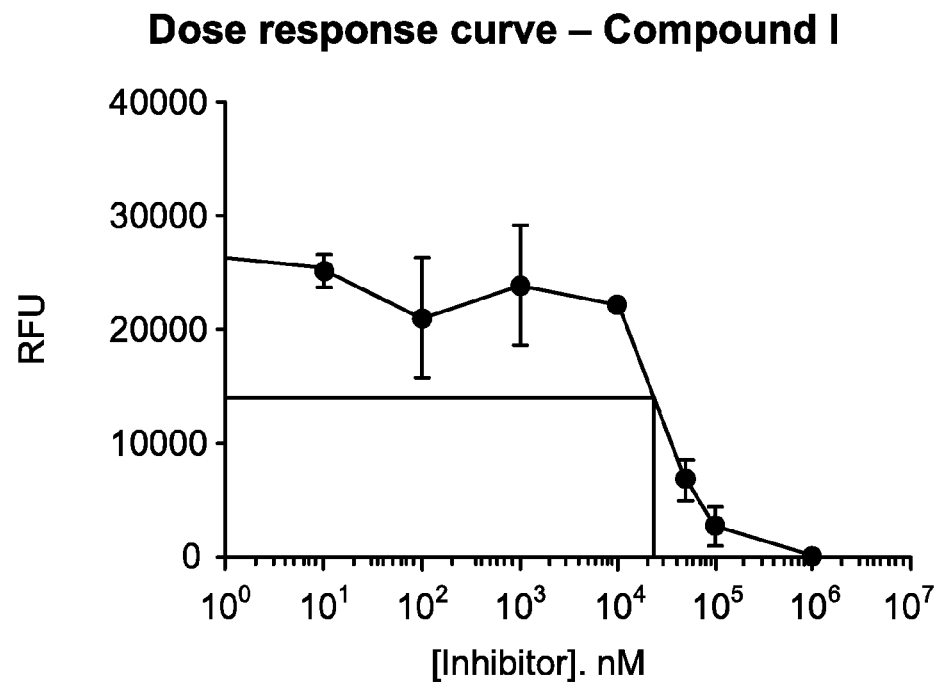
Figure 14C:
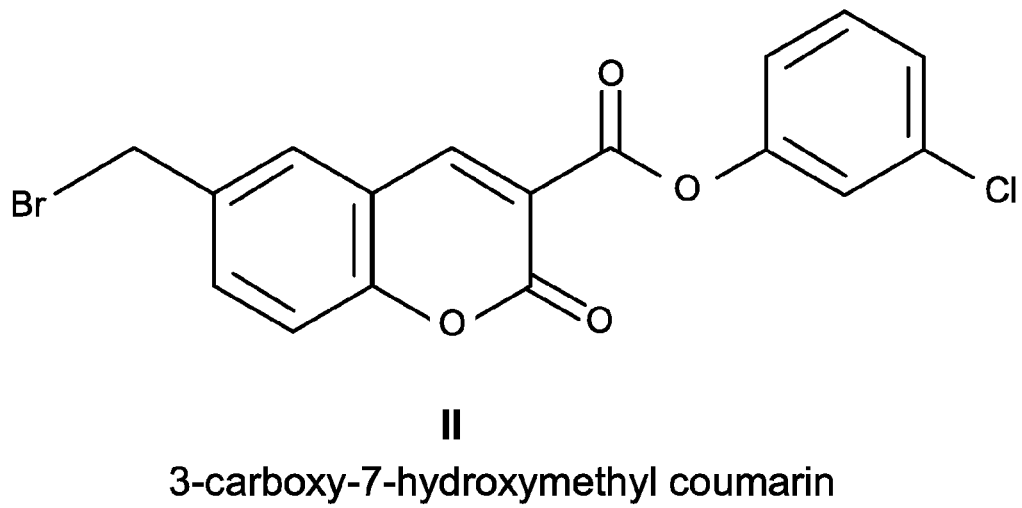
Figure 14D:
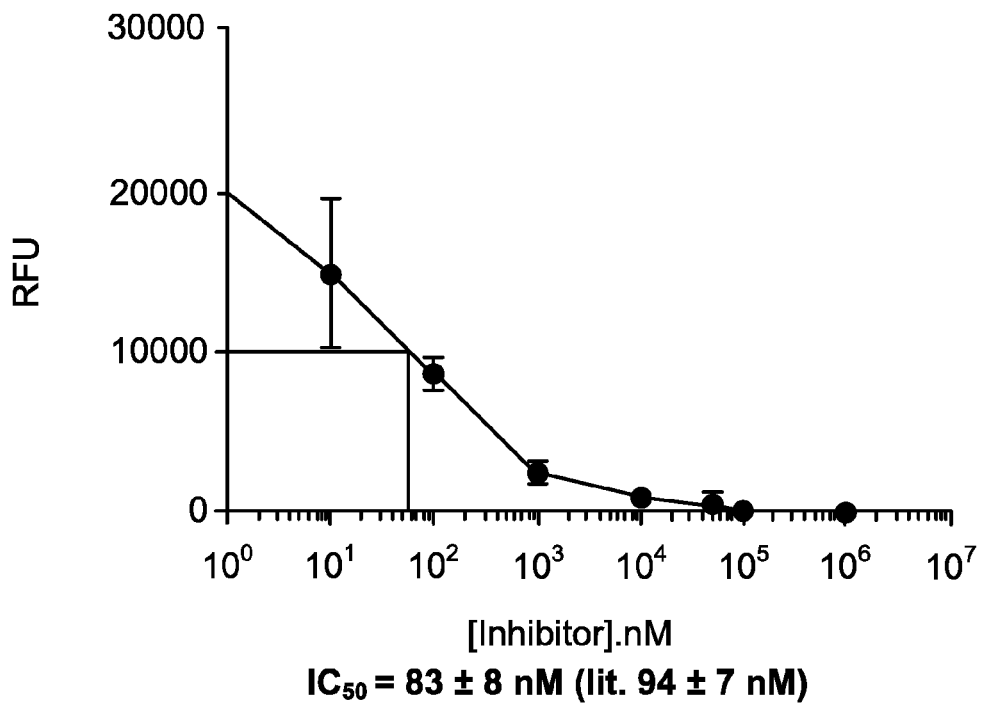

Two organic compounds were tested for their inhibition of KLK5. Compound I (3-(3-chlorophenyl)carboxy-7-hydroxymethyl coumarin) had an $IC_{50}$ value of 52±12 µM (FIGS. 14A and 14B). Compound II (3-carboxy-7-hydroxymethyl coumarin) had an $IC_{50}$ value of 83±8 nM (14C and 14D). Compound I and II were non reversible inhibitors.

Discussion

Figure 5A:
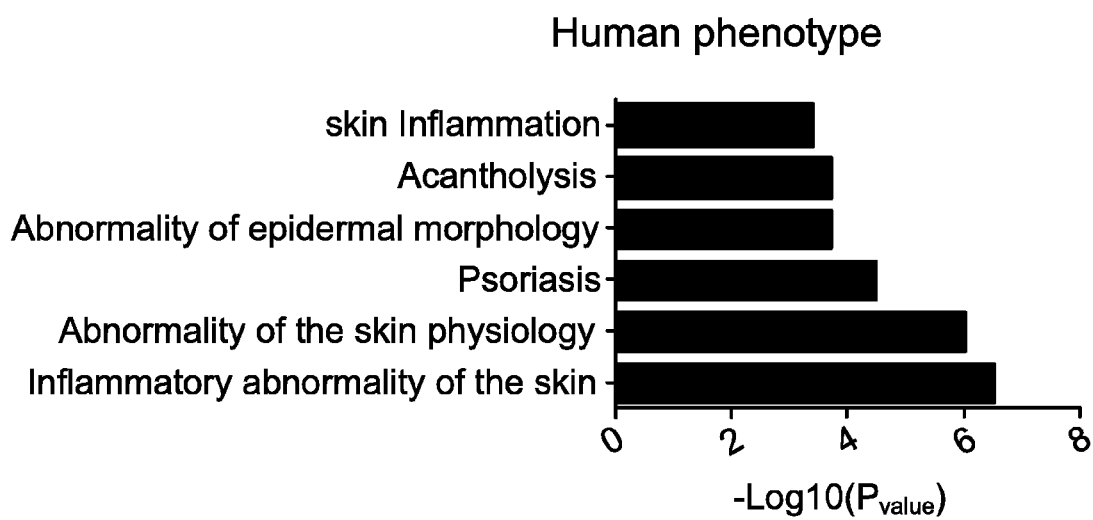
FIGS. 5A and 5B show that loss of SPINK7 induces inflamed esophageal mucosa transcriptome.
Figure 5B:
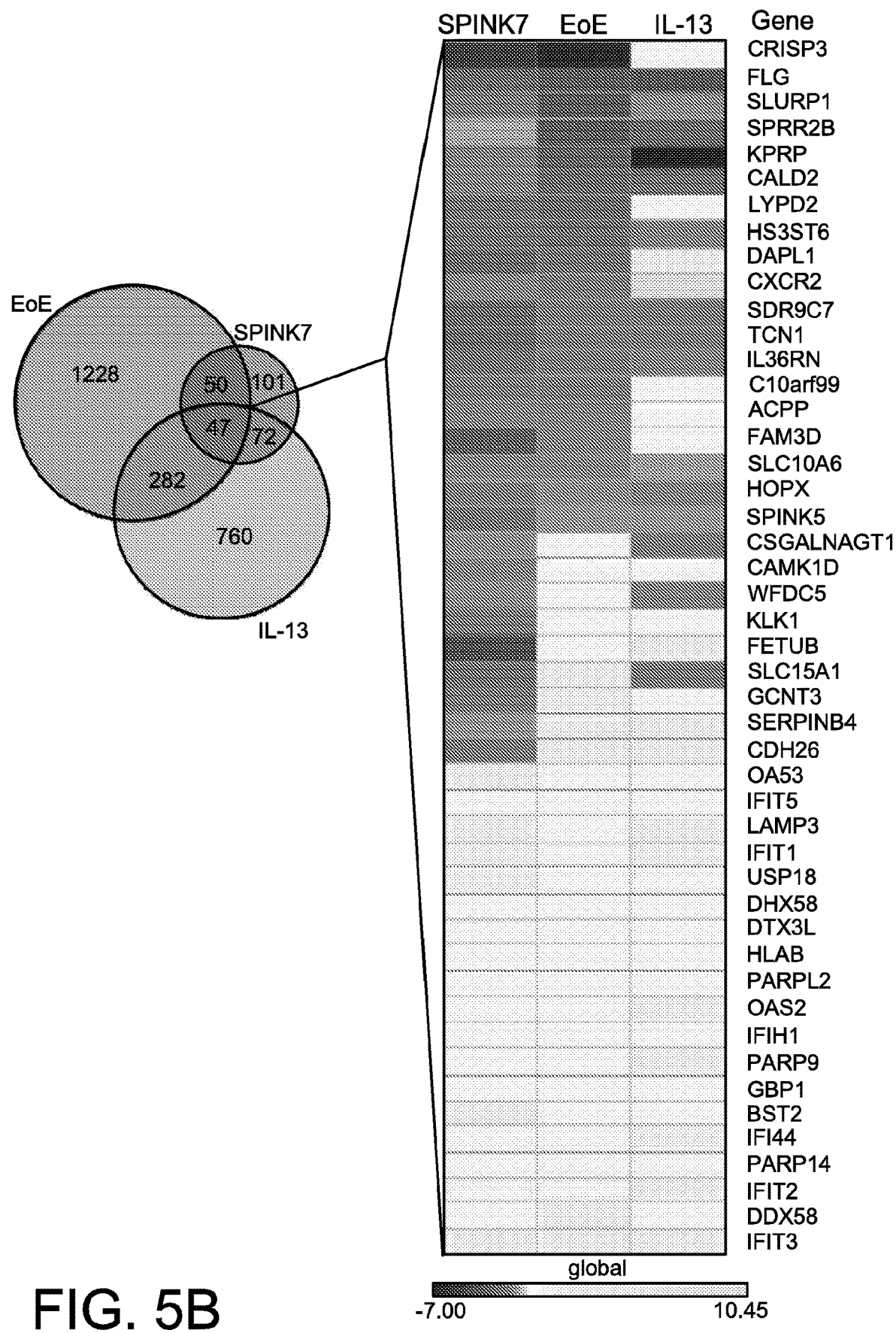

The data presented herein identify a role for the naturally occurring serine proteinase inhibitor SPINK7 as a key non-redundant checkpoint in regulating epithelial homeostatic responses in the esophagus (Summarized in FIG. 8). Multiple lines of evidence are presented showing that loss of SPINK7 is sufficient for induction of pro-inflammatory responses including:

(1) loss of barrier integrity including formation of dilated intercellular spaces (FIGS. 6A and 6B), absence of microplicae (FIG. 6C), increased paracellular permeability and reduced TEER (FIGS. 8A and 11B);

(2) epithelial acantholysis including disruption of the adherens junction proteins E-cadherin, β-catenin and DSG1 (FIG. 7);

(3) defective epithelial cell differentiation highlighted by loss of FLG expression (FIGS. 3A-3C and 4A and 4B);

(4) nuclear mobilization of NFATC1 and over-production of pro-inflammatory cytokines (FIG. 5A-5J FIGS. 9A-9C); and (5) induction of an innate transcript signature that overlaps with that associated with allergic inflammation (FIGS. 5A and 5B).

The known SPINK7 target uPA was identified as a mediator of the pathogenic events downstream from the loss of SPINK7 by demonstrating that uPA activity increased in the esophagus of EoE patients compared to control individuals, that uPA receptor was modulated in the esophagus, and that SPINK7 was an inhibitor of uPA, consistent with prior reports.

In addition, KLK5 was identified as a novel and direct target of SPINK7. These findings are stipulated by identifying genetic epistasis between SPINK7 and PLAU with two genes that are cardinal for Th2 immunity (i.e. ST2 and TSLP respectively; data not shown).

The relative importance of SPINK7 in the context of EoE, was demonstrated by its relative deficiency in EoE versus control individuals and its high expression in normal esophagus. Indeed, analysis of esophageal specific genes in the protein atlas revealed that SPINK7 was an esophageal enriched gene (Uhlen, M. et al. Proteomics. *Science* 347, 1260419 (2015)). Evidence is provided that loss of SPINK7 may be upstream from loss of SPINK5, which is undoubtedly contributory to the Th2-response, as demonstrated by its rare genetic deficiency (Netherton's syndrome) (Furio, L. et al. *The Journal of experimental medicine* 211, 499-513).

It is notable that SPINK7 was also known as esophageal cancer related gene 2 (ECRG2) as it was been identified as a tumor suppressor by its ability to inhibit the binding of uPA to uPAR and suppress cell migration/invasion and signaling pathways including elevated cytosolic calcium levels (Cheng, X., Lu, S. H. & Cui, Y. *Cancer letters* 290, 87-95 (2010), Huang, G. et al. *Carcinogenesis* 28, 2274-2281 (2007), Cheng, X., et al. *The Journal of biological chemistry* 284, 30897-30906 (2009), Brooks, A. M. et al. *American journal of respiratory cell and molecular biology* 35, 503-51 (2006), and Alfano, M., et al. *Journal of leukocyte biology* 74, 750-756 (2003)). The loss of SPINK7 in esophageal epithelial cells was demonstrated to increase uPA activity and that uPA activity is increased in the esophagus of EoE patients compared to controls (FIGS. 10A and 12B).

The expression of uPAR was markedly reduced in esophageal eosinophils compared to blood eosinophils (FIG. 12C), demonstrating its dynamic regulation during EoE. uPAR is known to be internalized following engagement of uPA: serpin complexes (Nykjaer, A. et al. *The EMBO journal* 16, 2610-2620 (1997)). Therefore, the reduction of uPAR expression on the cell surface of eosinophils represents local uPA hyperactivity. In addition, genetic epistasis between TSLP and PLAU (data not shown) providing independent evidence for the likely contribution of this pathway was demonstrated. These collective data sets indicated that SPINK7 mediated regulation of the uPA/uPAR complex was involved in disease pathogenesis. In addition, SPINK7 was able to specifically inhibit KLK5 in vitro which is remarkable as KLK5 is an upstream proteinase known to cleave and activate most members of the KLK family as well as uPA (Brattsand, M., et al *The Journal of investigative dermatology* 124, 198-203 (2005), Wang, S. et al. *Experimental dermatology* 23, 524-526 (2014), Furio, L. et al. *The Journal of experimental medicine* 211, 499-513, Debela, M. et al. *Biological chemistry* 389, 623-632 (2008), and Prassas, I., et al. *Nature reviews. Drug discovery* 14, 183-202 (2015)).

The possibility that loss of SPINK7 promoted NFAT activation was explored, because TSLP expression in keratinocytes is NFAT-dependent (Wilson, S. R. et al. *Cell* 155, 285-295 (2013)). Indeed, loss of SPINK7 promoted mobilization of NFATC1 to the nucleus and primed esophageal epithelial cells to release several major drivers of adaptive immunity such as GM-CSF, TNFα, and IL-8. The release of some of these cytokines was blocked by inhibiting NFAT activation by CsA and FK506.

Local fluctuations in SPINK7 expression serves a dual role in atopic reaction; firstly, by hampering the epithelial barrier which promote immune cells to encounter luminal antigens and secondly, by priming epithelial cells to secrete pro-allergic and immunomodulatory cytokines.

It has been reported that SPINK7 provides a spindle assembly checkpoint and that loss of SPINK7 results in rapid proliferation and chromosomal instability (Cheng, X., et al *The Journal of biological chemistry* 283, 5888-5898 (2008)). Therefore, the defect in the differentiation process caused by the loss of SPINK7 could be a part of programmed cell response to repair the damaged tissue by increasing the pool of undifferentiated cells with proliferative capacity.

In addition, the loss of SPINK7 caused release of several cytokines (i.e. IL-1β, TNFα and PDGF) that are key regulatory molecules of tissue repair (through uPA/uPAR-dependent mechanism) (Chabot, V. et al. *Stem cell research & therapy* 6, 188 (2015)), IL-8 is known to regulate tissue regeneration by promoting angiogenesis (Stewart, C. E., et al *Thorax* 67, 477-487 (2012)), and Alexander, R. A. et al. *Cardiovascular research* 94, 125-135 (2012)), and is increased in the esophagus of EoE patients (Persad, R. et al. *Journal of pediatric gastroenterology and nutrition* 55, 251-260 (2012) and Blanchard, C. et al. *The Journal of allergy and clinical immunology* 127, 208-217, 217 e201-207 (2011)).

This study identified a hitherto unrecognized pathway centrally mediated by SPINK7 and involving unleashed proteinase activity in allergic esophageal inflammation. Loss of SPINK7 and aberrant regulation of its downstream targets resulted in a defect in epithelial cell differentiation, loss of barrier function, and induction of an innate transcript signature that overlaps with allergic inflammation.

This pathway serves a causative role in compromising epithelial barrier and as an internal signal for epithelial damage with inflammatory consequences. SPINK7 provides a novel checkpoint for regulating a pro-inflammatory response characterized by excessive cytokine production and eosinophil infiltration in the esophagus. In addition, genetic variants in this pathway interact with undoubtedly atopic mechanisms (e.g. TSLP and IL-33/ST2) to initiate and propagate allergic inflammation at least in the esophagus.

Administration of the serine proteinase inhibitor, A1AT, was demonstrated to restore the epithelial impairment, at least in part; such that protein replacement therapy with proteinase inhibitors such as A1AT has therapeutic potential for atopic diseases such as EoE and Netherton's syndrome.

These data provide evidence that proteinases serve an important role in regulating immune response and substantiate the need to pursue therapeutic strategies that modulate relevant immune responses by suppression of uncontrolled proteinases in disease pathophysiology.

What is claimed is:

1. A method of treating an allergic inflammatory condition in a subject in need thereof, the allergic inflammatory condition characterized by inflammation of a squamous epithelium in a target tissue of the subject, the method comprising administering to the subject a pharmaceutical composition comprising an amount of alpha-1 proteinase inhibitor effective to replenish SPINK7 protein and/or SPINK7 anti-proteinase activity in the target tissue, wherein the alpha-1 proteinase inhibitor is the only therapeutic agent administered to the subject.

2. The method of claim 1, wherein the allergic inflammatory condition is esophageal eosinophilia (EE).

3. The method of claim 2, wherein the allergic inflammatory condition is eosinophilic esophagitis (EoE).

4. The method of claim 3, wherein the method further comprises subjecting the subject to a dietary modification to eliminate one or more potential food allergens.

5. The method of claim 3, wherein the subject is human.

6. The method of claim 1, wherein the subject is human.

* * * * *

UNITED STATES PATENT AND TRADEMARK OFFICE
CERTIFICATE OF CORRECTION

| | |
|---|---|
| PATENT NO. | : 10,821,094 B2 |
| APPLICATION NO. | : 16/069412 |
| DATED | : November 3, 2020 |
| INVENTOR(S) | : Nurit P. Azouz et al. |

It is certified that error appears in the above-identified patent and that said Letters Patent is hereby corrected as shown below:

In the Specification

Under the Cross Reference to Related Application Paragraph
Column 1, please add:
-- GOVERNMENT SUPPORT CLAUSE
This invention was made with Government support under contract AI070235 awarded by the National Institutes of Health. The Government has certain rights in the invention. --

Signed and Sealed this
Eighth Day of October, 2024

Katherine Kelly Vidal
*Director of the United States Patent and Trademark Office*